(12) United States Patent
Tegg et al.

(10) Patent No.: US 12,721,975 B2
(45) Date of Patent: Sep. 1, 2026

(54) SPLITTABLE SHEATH

(71) Applicant: St. Jude Medical, Cardiology Division, Inc., St. Paul, MN (US)

(72) Inventors: Troy T. Tegg, Elk River, MN (US); Derek C. Sutermeister, Ham Lake, MN (US); Bruce Ebner, Shorewood, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 875 days.

(21) Appl. No.: 17/438,326

(22) PCT Filed: Mar. 14, 2020

(86) PCT No.: PCT/IB2020/052342
§ 371 (c)(1),
(2) Date: Sep. 10, 2021

(87) PCT Pub. No.: WO2020/183438
PCT Pub. Date: Sep. 17, 2020

(65) Prior Publication Data

US 2022/0184348 A1 Jun. 16, 2022

Related U.S. Application Data

(60) Provisional application No. 62/818,743, filed on Mar. 14, 2019.

(51) Int. Cl.
*A61B 5/287* (2021.01)
*A61B 5/29* (2021.01)
(Continued)

(52) U.S. Cl.
CPC ......... *A61M 25/0668* (2013.01); *A61B 5/287* (2021.01); *A61B 5/29* (2021.01);
(Continued)

(58) Field of Classification Search
CPC .......... A61M 25/0668; A61M 25/0662; A61M 2025/0681; A61B 2560/066;
(Continued)

(56) References Cited

U.S. PATENT DOCUMENTS 4,801,294 A * 1/1989 Okada .................. A61M 25/02 604/161
4,983,168 A * 1/1991 Moorehead ....... A61M 25/0668 604/161

(Continued)

FOREIGN PATENT DOCUMENTS

WO 01/00268 A1 1/2001
WO 03/090835 A1 11/2003

(Continued)

OTHER PUBLICATIONS

First Office Action from related Chinese Patent Application No. 202080017642.6 mailed on Aug. 14, 2023 (20 pages including translation).

(Continued)

*Primary Examiner* — Darwin P Erezo
*Assistant Examiner* — Mitchell Brian Hoag
(74) *Attorney, Agent, or Firm* — WOMBLE BOND DICKINSON (US) LLP

(57) ABSTRACT

A splittable sheath for an implantable medical device can include a jacket having an outer diameter and an inner diameter. A lumen can be defined by the inner diameter and extended from a proximal end to a distal end of the jacket. An electrode can be located at the distal end of the jacket. A signal wire can be disposed within the jacket and can be electrically coupled to the electrode. A rail can be configured to shield the signal wire from a cut path of a sheath splitter. In some examples, the sheath can further include a second rail. For instance, the signal wire can be located between a
(Continued)

first rail and a second rail along the length of the sheath. The cut path can be located between the first rail and the second rail on a radially opposing side of the sheath from the signal wire.

23 Claims, 17 Drawing Sheets

(51) Int. Cl.
*A61M 25/06* (2006.01)
*A61N 1/05* (2006.01)

(52) U.S. Cl.
CPC .......... *A61N 1/056* (2013.01); *A61B 2505/05* (2013.01); *A61B 2560/066* (2013.01)

(58) Field of Classification Search
CPC ..... A61B 17/3468; A61B 90/11; A61N 1/056; A61N 1/0563; A61N 1/0565; A61N 1/0568; A61N 1/057; A61N 1/0573; A61N 1/0575; A61N 2001/0578; A61N 2001/058; A61N 2001/0582; A61N 1/059; A61N 1/0592; A61N 1/0595; A61N 1/0597
USPC .......................................................... 606/129
See application file for complete search history.

(56) References Cited

U.S. PATENT DOCUMENTS 5,507,766 A * 4/1996 Kugo .................. A61M 25/104 606/95
6,979,312 B2 12/2005 Shimada
7,263,397 B2 8/2007 Hauck et al.
7,386,339 B2 6/2008 Strommer et al.
7,497,844 B2 * 3/2009 Spear ................ A61M 25/0147 604/164.11
8,142,446 B2 * 3/2012 Shan ................. A61M 25/0662 606/129
9,974,938 B2 * 5/2018 Pepin ................ A61M 25/0668
10,835,629 B2 * 11/2020 Lyons ................ A61C 17/0202
11,103,127 B2 * 8/2021 Sekowski ................ A61B 1/05
11,540,703 B2 * 1/2023 Sekowski ................ A61B 1/07
12,285,278 B2 * 4/2025 Breslich ............. A61B 17/0401
12,324,883 B2 * 6/2025 Traxler ................. A61M 25/10
12,458,400 B2 * 11/2025 Holbrooks ......... A61B 17/4241
2002/0072787 A1 * 6/2002 Partridge ............. A61N 1/0573 607/122
2003/0212373 A1 * 11/2003 Hall .................. A61M 25/0668 604/263
2003/0229386 A1 * 12/2003 Rosenman ............. A61N 1/056 607/116
2005/0085746 A1 * 4/2005 Adams .............. A61M 25/0662 600/585
2005/0149155 A1 * 7/2005 Scheiner ................ A61N 1/057 607/9
2006/0122676 A1 6/2006 Ko et al.
2008/0281390 A1 * 11/2008 Marshall ................ A61N 1/056 607/116
2010/0094225 A1 4/2010 Hastings et al.
2011/0071537 A1 * 3/2011 Koga ...................... A61F 2/389 606/88
2012/0035585 A1 * 2/2012 Kurrus .............. A61M 25/0668 604/171
2012/0046722 A1 * 2/2012 Olsen .................. A61N 1/3752 607/116
2012/0157854 A1 * 6/2012 Kurrus ................ A61M 25/065 604/164.01
2014/0276432 A1 * 9/2014 Bierman ........... A61M 25/0097 604/167.03
2015/0080851 A1 * 3/2015 Kurth ........................ C11B 3/04 604/506
2016/0220741 A1 * 8/2016 Garrison ........... A61M 25/0054
2016/0317800 A1 * 11/2016 Barker ..................... A61N 1/05
2017/0238965 A1 * 8/2017 Murphy .............. A61M 60/148
2018/0185094 A1 * 7/2018 Harlan .............. A61M 25/0029
2018/0289925 A1 * 10/2018 Palmer .............. A61M 25/0043
2019/0224458 A1 * 7/2019 Morero ................... A61L 29/06
2019/0224459 A1 * 7/2019 Pedroni ................. A61M 25/10
2021/0031006 A1 * 2/2021 Subramaniam ... A61M 25/0136
2021/0069403 A1 * 3/2021 Yevzlin .................. A61B 17/11
2021/0228844 A1 * 7/2021 Ogle ..................... A61M 25/09

FOREIGN PATENT DOCUMENTS

WO 2012/121817 A1 9/2012
WO 2019/161286 A1 8/2019

OTHER PUBLICATIONS

Notice of Allowance from related Chinese Patent Application No. 202080017642.6 mailed on Mar. 27, 2024 (5 pages including translation).
Extended European Search Report for related EP Application No. 24175301.1 mailed on Sep. 4, 2024, 07 pages.
Communication pursuant to Article 94(3) EPC (office action) dated May 15, 2026 from related European Patent Application No. 24175301.1, 4 pages.

* cited by examiner

136
A
A
166
140
148
162B
B
B
158B
102
162A
168
C
C
158A
128B
128A 136
166
158A 162A
148
102
140
168
128A
128B

γ1
Φ1
162A
158A
148
134
α1
164
158B
102
162B
166

128A
128B
1882
168
158A
162A
148
162B
158B
102
136

1882
128A
128B
168
162A
158A
162B
148
158B
102
136

SPLITTABLE SHEATH

BACKGROUND a. Field

The present disclosure relates to a splittable sheath used for navigating a placing an implantable device within a patient.

b. Background Art

Cardiac rhythm management systems are useful for electrically stimulating a patient's heart to treat various cardiac arrhythmias. The current standard of care is to pace the right ventricle by myocardial stimulation. In this technique, pacemaker leads are placed at the apex of the right ventricle and at the AV node, the coronary sinus or the left ventricle, and a pacemaker sends electrical pulses to these areas of the heart. While effective, this technique can cause abnormal electrical activation sequences resulting in mechanical ventricular dyssynchrony and an increased risk of heart failure, atrial fibrillation and overall mortality.

An alternative approach has been proposed in which an electrode lead is placed into the bundle of His located either in the septal wall of the right atrium or subvalvular from the right ventricle also in the atrial septum. As part of the electrical conduction system of the heart, the bundle of His transmits electrical impulses from the atrioventricular (AV) node to the ventricles of the heart. As the electrical impulses that regulate the heartbeat are conducted through the bundle of His from the right atrium to the left and right ventricles, a lead placed in or in close proximity to the bundle of His would enable the entire electrical conduction system to be paced in a physiologically natural way. Pacing the ventricles in this manner, which closely mimics normal AV conduction, can greatly reduce or eliminate the risks associated with traditional CRT pacing.

While the improved results obtainable with His pacing have been recognized, in practice His pacing is difficult to achieve because the bundle of His is very small and difficult to locate and access with available devices. The bundle of His has a nominal length of about 5 mm and a nominal width of about 2 mm. It generates an electrical signal that is a small fraction of that generated by the ventricles. As a result of its small size and weak electrical signal, the bundle of His is extremely difficult to find with a conventional pacing lead. Moreover, once the bundle of His has been located, it is difficult to maintain the position of the lead while it is being affixed to the cardiac tissue. The difficulties involved in locating the bundle of His and affixing a pacing lead thereto are reflected in the time it takes to implant the leads of an electrical stimulation device, such as a pacemaker. In a typical case, implanting biventricular leads can be completed in as little as 1 minute. To the contrary, the placement of a single lead for His pacing may take 30 minutes or more, frequently without success. In those cases, the physicians typically revert to conventional lead placement.

Once the lead is placed and affixed to the tissue, the sheath can be withdrawn from the patient and removed from the lead. To remove the sheath from the lead a blade can split the sheath along a longitudinal direction. The blade can cut the sheath from a proximal end to a distal end. The cut is often performed as the sheath is withdrawn from the body. Often, the travel of the blade can be unpredictable or irregular. In some instances, the blade could cut through various wires or liners within the sheath. Accordingly, an electrical connection can be degraded or severed. In other instances pieces of wire or liner can be severed from the sheath creating debris. In some examples, debris could enter the patient, for instance, the debris could fall into an incision through which the sheath is inserted into the body. Due to manufacturing constraints, internal elements of the sheath are not always sterilized.

There is therefore a need for improvements to the devices used to deliver and implant electrode leads to reduce the formation of debris generated from separating the sheath from the lead. The foregoing discussion is intended only to illustrate the present field and should not be taken as a disavowal of claim scope.

BRIEF SUMMARY

The instant disclosure relates to a splittable sheath for an implantable medical device for treatment or diagnosis of cardiac arrhythmias via, for example, a steerable sheath for guiding and delivering an implantable lead to a target location within a patient. In some examples, the sheath can include one or more electrodes for identifying a fixation site along the tissue. In general, a tip portions of the lead can comprise an anchor to fixate the lead to the tissue (e.g., a beating heart wall). The sheath can include various separation means, as described further herein, for removing the sheath from the lead when the lead is fixated to the tissue. The lead can be used to deliver cardiac resynchronization therapy (CRT) to the heart.

In an example a splittable sheath for an implantable medical device can include a jacket having an outer diameter and an inner diameter. A lumen can be defined by the inner diameter and can be extended from a proximal end to a distal end of the jacket. An electrode can be located at the distal end of the jacket. A signal wire can be disposed within the jacket and electrically coupled to the electrode. A rail can be configured to shield the signal wire from a cut path of a sheath splitter.

In some examples, the sheath can further include a second rail. For instance, the rail can be a first rail, and the signal wire can be located between the first rail and the second rail along the length of the sheath. The cut path can be located between the first rail and the second rail on a radially opposing side of the sheath from the signal wire. At the proximal end of the jacket, the first rail can be located at a radial offset of greater than 270 degrees from the second rail. At the distal end of the jacket, the first rail is located at a radial offset of less than 90 degrees from the second rail. In an example, a cut zone can be defined between the first rail and the second rail on a radially opposing side of the sheath from the signal wire. The cut zone at the proximal end of the jacket can be larger than at the distal end of the jacket. In an example, the rail can be exposed from the jacket at the proximal end.

In various examples, the rail can be constructed from a cut resistant material. For instance, the rail is constructed from stainless steel. The rail can be configured to reduce debris formation caused by contact with the sheath splitter. For example, the rail can include a solid cross section.

In some examples, the signal wire can be located at a bend plane along the cross section of the sheath. In various examples, the jacket can include a jacket stripe extended from the proximal end to the distal end. In an example, the jacket stripe can be constructed from a material that is softer than a material of the jacket. In some examples, the jacket can include two jacket stripes extended from the proximal end to the distal end. In an example, the jacket stripe can be more cut resistant than a material of the jacket.

In an example, the radial locations of the signal wire and the rail can remain constant along the length of the sheath. In some examples, the splittable sheath can include a pull wire disposed within the jacket. The rail can be further configured to shield the pull wire from the cut path. In an example, the splittable sheath can include a lead disposed within the lumen of the sheath.

In some examples, a splittable sheath can include a jacket including an outer diameter and an inner diameter. A lumen can be defined by the inner diameter and extended from a proximal end to a distal end of the jacket. An electrode can be located at the distal end of the jacket. A signal wire can be disposed within the jacket and electrically coupled to the electrode. The splittable sheath can include a first rail and a second rail each configured to shield the signal wire from a cut path of a sheath splitter. The signal wire can be located between the first rail and the second rail along the length of the sheath. The cut path can be located between the first rail and the second rail on a radially opposing side of the sheath from the signal wire.

In a further example, a method for making a splittable sheath can include placing a lead liner over a lumen mandrel and placing a signal wire liner over a signal wire mandrel. A first rail mandrel and a second rail mandrel can be located along an outer diameter of the lead liner. The signal wire liner can be located between the first rail mandrel and the second rail mandrel along the length of the sheath. A jacket can be applied over the signal wire liner and the first and second rail mandrels. Each of the lumen mandrel, the signal wire mandrel, and the first and second rail mandrels can be removed after the jacket is applied. A signal wire can be inserted into the signal wire liner lumen, a first rail can be inserted into the first rail lumen, and a second rail can be inserted into the second rail lumen, after the lumen mandrel, the signal wire mandrel, and the first and second rail mandrels are removed. The signal wire can be electrically coupled to an electrode located on a distal end of the jacket.

In an example, the method can include disposing a braid around the signal wire liner and the first and second rail mandrels before applying the jacket. The jacket can be extruded over the braid. In another example, applying the jacket can include placing an extruded profile over the signal wire liner, the first and second rail mandrels, and the lead liner. In an example, the extruded profile can be heated to fuse the profile around the signal wire liner, the first and second rail mandrels, and the lead liner. In a further example, applying the jacket can include applying a jacket including a jacket stripe. The jacket stripe can include a different material than the jacket. In some examples, placing the signal wire lumen can include placing the signal wire lumen along a bend plane of the sheath. In an example, inserting the first rail and the second rail can include inserting a first rail and a second rail that are constructed of a solid material to reduce debris formation. For instance, the first rail lumen and the second rail lumen can be unlined and the first rail and the second rail can be uncoated.

The foregoing and other aspects, features, details, utilities, and advantages of the present disclosure will be apparent from reading the following description and claims, and from reviewing the accompanying drawings.

DETAILED DESCRIPTION OF EMBODIMENTS

Several embodiments of catheter delivery systems, such as catheter delivery systems including steerable sheaths for guiding and delivering implantable leads are disclosed herein. Sheaths can include one or more electrodes for identifying a fixation site along the tissue. In general, the tip portions of the lead can comprise an anchor to fixate the lead to the tissue (e.g., a beating heart wall). The sheaths can include various separation means, as described herein, for removing the sheath from the lead when the lead is fixated to the tissue. Details of the various embodiments of the present disclosure are described below with specific reference to the figures.

Figure 1:
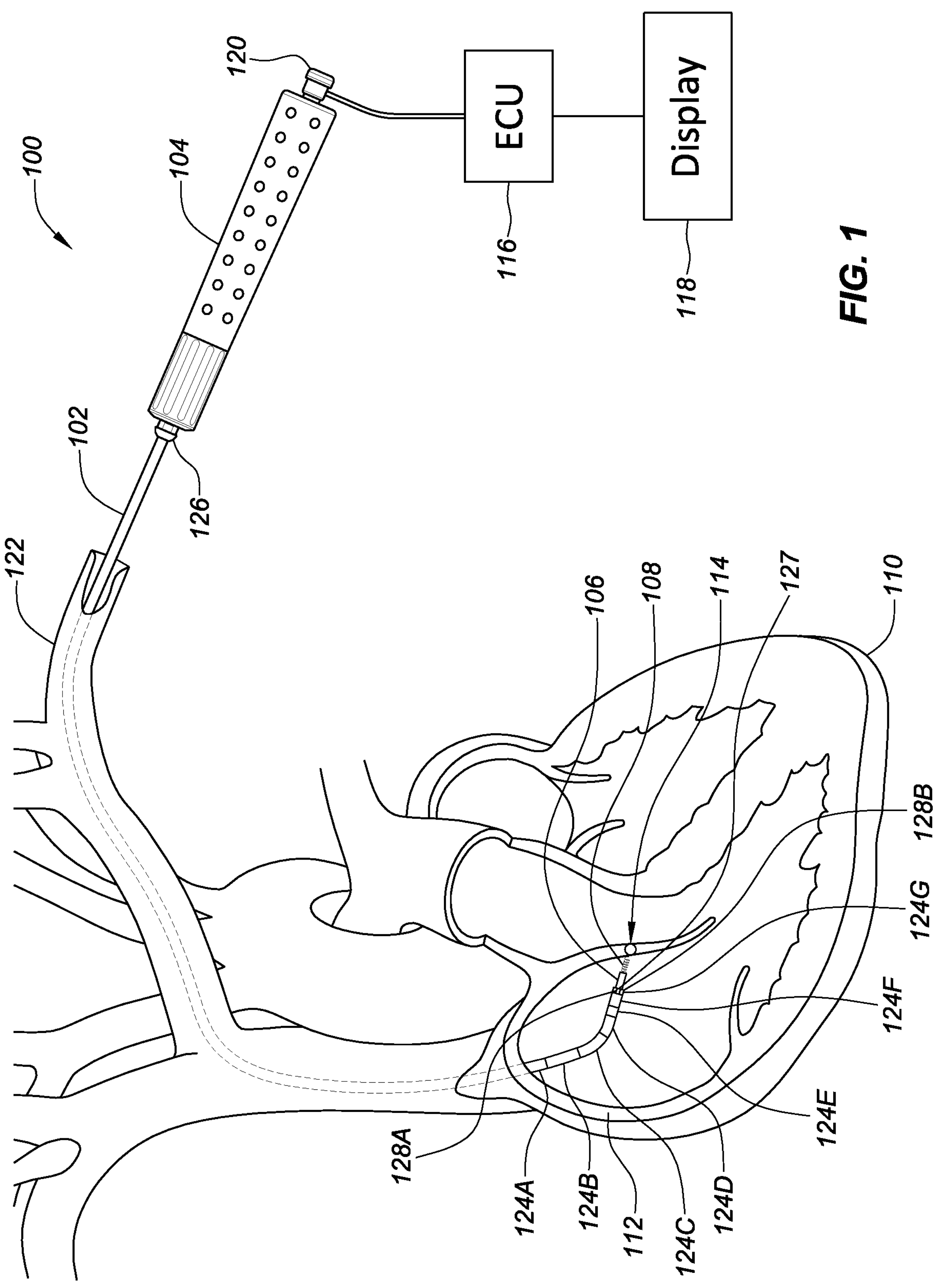
FIG. 1 depicts an example of a catheter delivery system.

FIG. 1 depicts a catheter delivery system 100 including a handle 104, a sheath 102 operatively coupled to the handle 104, and a lead 106 disposed within a lumen of the sheath 102. In the example shown in FIG. 1, the lead 106 can be navigated by the sheath 102 through the subclavian vein 122 and the superior vena cava into the right atrium 112 of the heart 110. In an example, the lead 106 can be used to deliver cardiac resynchronization therapy (CRT) to the heart 110. For instance, the lead 106 can be a cardiac pacing lead. The distal end 127 of the lead 106 can be fixated to the tissue, and the proximal end of the lead 106 can be operatively coupled to a cardiac resynchronization device (CRD). For instance, the distal end of the lead 106 can include an anchor 108, such as a helical fixation screw, fixation barbs, or other fixation means. In some examples, the electrodes 128A, B can be in contact with the tissue or in other examples the electrodes 128A and 128B can detect near-field electrophysiological signals from the heart 110 to detect a location of the distal end 127 of the sheath 102 using electrophysiological signals, such as electrogram or electrocardiogram signals. Although the example of FIG. 1 depicts the catheter delivery system 100 for use with placement of a CRT lead, it should be understood in other examples, however, that the system 100 can find application in connection with a wide variety of medical devices used within the body for diagnosis or treatment.

The electrodes 128A, B of the sheath 102 can be used to locate a fixation point along the tissue (e.g., the heart 110). In an example, the electrodes 128A, B can be used to detect a location of the His bundle 114 within the right atrium 112. The electrodes 128A, B can be located on diametrically opposed sides of the distal end 127 of the sheath 102. The sheath 102 can be manipulated to advance the electrodes 128A, B along the atrial wall until the faint electrical signals from His bundle 114 are identified. This typically occurs when electrodes 128A and 128B are on opposite sides of the His bundle 114. At this point, the sheath 102 can be manipulated to implant the anchor 108 in the atrial wall. As part of the electrical conduction system of the heart 110, the bundle of His 114 transmits electrical impulses from the atrioventricular (AV) node to the ventricles of the heart 110. As the electrical impulses that regulate the heartbeat are conducted through the bundle of His 114 from the right atrium 112 to the left and right ventricles, placing the lead 106 in or in close proximity to the bundle of His 114 would enable the entire electrical conduction system to be paced in a physiologically natural way. Pacing the ventricles in this manner, which closely mimics normal AV conduction within the heart 110 and can greatly reduce or eliminate the risks associated with traditional CRT pacing.

The sheath 102 can include a jacket comprising a polymer, such as a thermoplastic elastomer, such as a polyether block amide (e.g., sold under the name Pebax® by Arkema France). The jacket can provide columnar strength in the proximal and middle portions of sheath 102 and deflectability in the distal portion of the sheath 102.

The distal portion of the sheath 102 can include various interposing sections, such as sections 124A-G as shown in the example of FIG. 1. The sections 124A-G can include materials having different material properties, such as materials having different moduli of elasticity, moduli of flexure, or hardness to provide one or more hinge points along the lead 106. For instance, in the example of FIG. 1 the section 124A can include material having a durometer of 75; sections 124B, D, and F can include a material having a durometer of 55; sections 124C, E can have a durometer of 35; and the distal section 124G can have a durometer of 40.

Figure 3:
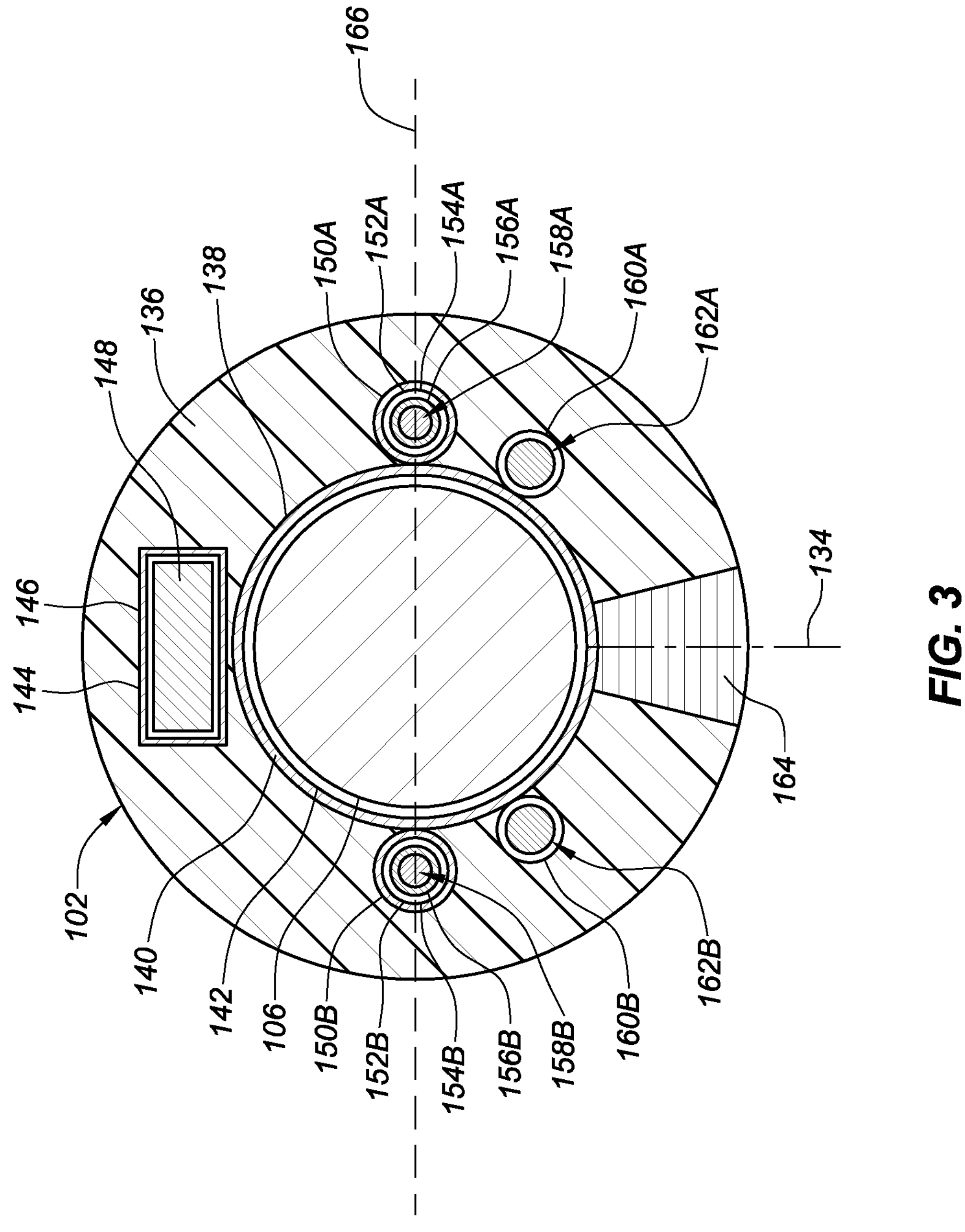
FIG. 3 depicts a cross-section of the sheath including a lead inserted within a lumen of the sheath.

Each of the various sections 124A-G can be joined to one or more of the other respective sections 124A-G by gluing, ultrasonic welding, reflow heating, or other techniques. In a preferred arrangement, the distal section 124G can be formed from a polymer that is softer than the material of sections 124A, B, D, F so as to provide an atraumatic tip to the sheath 102. In some embodiments, the polymers forming sections 124A-G may include radiopaque fillers, such as barium sulfate, tungsten, bismuth trioxide, bismuth subcarbonate, bismuth oxychloride and the like. Polymers containing the radiopaque filler can be used in one or more of the various sections 124A-G of the sheath 102. A lumen, as shown in the example of FIG. 3 and described further herein, can extend continuously through sheath 102 from distal end 127 to the handle 104. The lumen can include a diameter that is slightly larger than the diameter of the lead 106. For example, for a 7 French pacing lead (having a diameter of about 2.33 mm) the lumen may have a size of about 7.5 French (a diameter of about 2.5 mm).

The catheter delivery system 100 can include a handle 104, a sheath connector 126 at a first end of the handle 104, and an interface 120. The handle 104 can be used for steering or guiding the sheath 102, lead 106, or the combination thereof within a patient's body. For example, the handle 104 can include means to change the length of one or more pull wires extending through the sheath 102, lead 106, or both from the handle 104 to the distal end 127 of sheath 102. For instance, the handle 104 can include a rotary actuator that operatively engages with the sheath 102, the lead 106, or both to steer the sheath 102 or the lead 106 using one or more pull wires or to extend or retract the sheath 102, the lead 106, or combinations thereof.

In an example, the connector 126 can include a hemostasis valve. The sheath 102 can pass through the connector 126, which provides a seal to minimize blood loss from around the sheath 102. The interface 120 can be and electrical connector for communicatively coupling electrodes, sensors, or other electrical or electromechanical devices of the sheath 102, the lead 106, or the handle 104 to an electronic control unit (ECU) 116. In a further example, the interface 120 can include or can be combined with a hemostasis valve for communicating fluid to or from the sheath 102 or the lead 106. For instance, the handle 104 can include a conduit for connection to a source of flushing fluid. The conduit can travel through handle 104 for supplying the flushing fluid to flush the lumen of the sheath 102.

In some examples, a channel can be formed in the upper surface of the handle 104. The channel can be adapted to receive a sheath slitter including a blade for slitting sheath 102 following the insertion of the lead 106 in a patient, as will be explained more fully below.

In some examples, the catheter delivery system 100 can include an electronic control unit (ECU) 116 and a display 118. The ECU 116 can include, but is not limited to, a central processing unit (CPU), graphics processing unit (GPU), microprocessor, application specific integrated circuit (ASIC), a field programmable gate array (FPGA), complementary metal-oxide-semiconductor (CMOS), or the like. In some examples, the ECU can include memory, such as random-access memory (RAM), read-only memory (ROM), programmable read-only memory (PROM), erasable programmable read-only memory (EPROM), and electrically erasable programmable read-only memory (EEPROM), dynamic random-access memory (DRAM), static random-access memory (SRAM), Flash memory, or the like.

The ECU 116 can provide a means for controlling the operation of various components of the catheter delivery system 100. In an example, the ECU 116 can also provide a means for detecting electrophysiology characteristics (e.g., signals) from the tissue, the position and orientation of the sheath 102 or the lead 106 relative to the tissue and the body. The ECU 116 can also provide a means for generating display signals used to control the display 118.

The display 118 can convey information to a physician to assist in lead placement, diagnosis, treatment, or combinations thereof. The display 118 can comprise one or more conventional computer monitors or other display devices. The display 118 can present a graphical user interface (GUI) to the physician. The GUI can include a variety of information including, for example, an image of the geometry of the tissue, electrophysiology data (e.g., signals) associated with the tissue, graphs illustrating voltage levels over time for various electrodes, and images of the sheath 102 or lead 106, and other medical devices and related information indicative of the position of the sheath 102 or lead 106 and other devices relative to the tissue.

The catheter delivery system 100 can be used in conjunction with and electric-field-based positioning system or a magnetic-field-based positioning system to determine the position of the sheath 102 or the position of the lead 106 within the body. For instance, the catheter delivery system 100 can be combined with, for example, the EnSite™ NavX™ system sold by St. Jude Medical, Inc. of St. Paul, Minnesota, and described in, for example, U.S. Pat. No. 7,263,397 titled "Method and Apparatus for Catheter Navigation and Location Mapping in the Heart," the entire disclosure of which is hereby incorporated by reference as though fully set forth herein. In an example, the catheter delivery system 100 can be combined with, for example, the EnSite Precision™ system sold by St. Jude Medical, Inc., of St. Paul, Minnesota. In other examples, the catheter delivery system 100 can be combined with the GMPS system made available by MediGuide, Ltd. and generally shown and described in, for example, U.S. Pat. No. 7,386,339 titled "Medical Imaging and Navigation System," the entire disclosure of which is hereby incorporated by reference as though fully set forth herein.

In some examples, the catheter delivery system 100 can be combined with, for example, the mapping guide sheath, splitter, handle, and implantable cardiac pacing system described in, for example, PCT application number PCT/US2019/018329 titled "Deflectable Mapping Guide Sheath for His Bundle Pacing," the entire disclosure of which is hereby incorporated by reference as though fully set forth herein.

In further examples, the catheter delivery system 100 can be combined with, the steerable catheter of U.S. Pat. No. 6,979,312 titled "Steerable Sheath Catheters," the entire disclosure of which is hereby incorporated by reference as though fully set forth herein.

Figure 2:
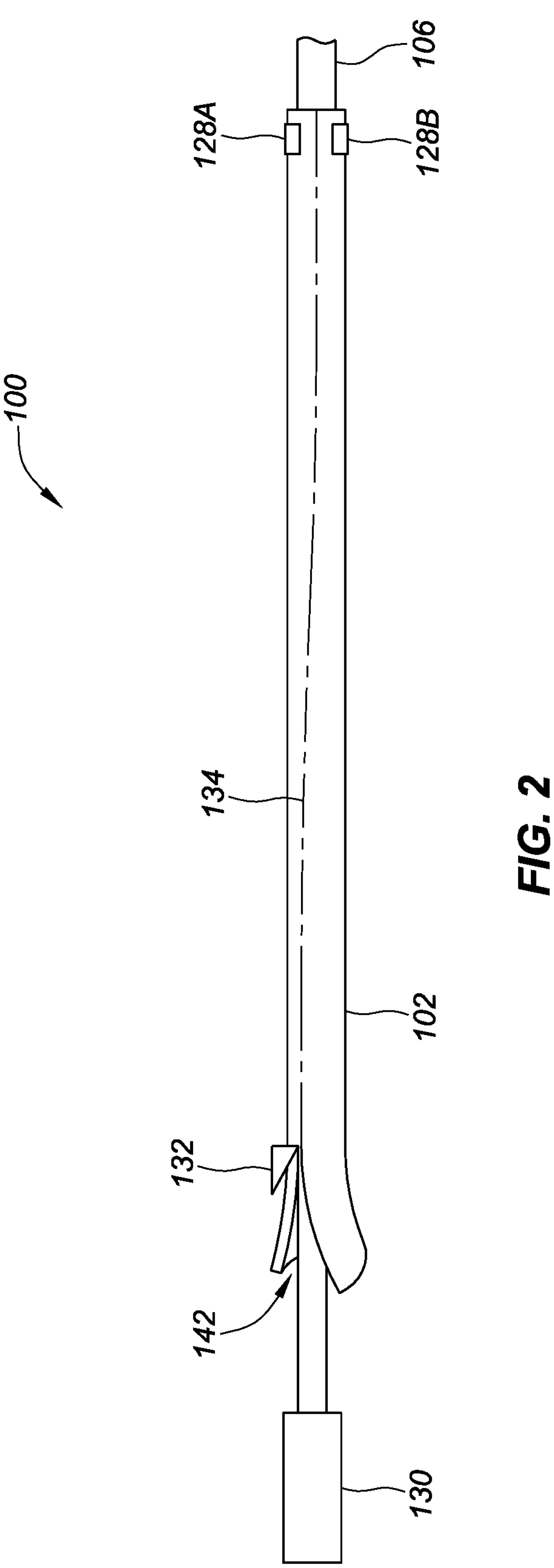
FIG. 2 illustrates an example of a splittable sheath with a lead extending through a lumen of the sheath.

FIG. 2 illustrates an example of the splittable sheath 102 with the lead 106 extending through the lumen (e.g., lumen 142) of the sheath 102. In this example the distal end of the lead 106 can be fixated to the tissue. The proximal end of the lead 106 can include a connector 130. In an example, the electrical connector 130 can be electrically coupled to a CRT device. Once the lead 106 is fixated, the sheath 102 can be withdrawn from the patient. In some examples, the lumen 142 of the sheath 102 can include a diameter that is the same size, nearly the same size, or smaller (e.g., interference fit) than the diameter of the lead 106 in order to facilitate a compact design for navigation through the body. The reduced (e.g., minimal or lack of) clearance between the lumen 142 and the lead 106 can also provide for more precise delivery of the lead 106 as there is less clearance for the lead 106 to shift within the lumen 142. As result, the sheath 102 may not be removable from the lead 106 by sliding the sheath 102 over the lead connector 130. To remove the sheath 102 from the lead 106, a blade 132 can split the sheath along a longitudinal direction. As shown in the example of FIG. 2, the blade 132 can follow a cut path 134. The cut path 134 can extend from the proximal end of the sheath 102 to the distal end of the sheath 102 and between the electrodes 128A and 128B. For example, the blade 132 can cut through a thickness of the sheath 102 between an outer diameter and an inner diameter of the sheath 102. The cut can be performed as the sheath 102 is withdrawn from the body. As previously described, the blade 132 can be included in a sheath slitter. The sheath slitter can be coupled to a channel of the handle 104.

FIG. 3 depicts a cross-section of the sheath 102 including the lead 106 inserted within the lumen of the sheath 102. A jacket 136 of the sheath 102 can include a jacket lumen 138. A lead liner 140 can be located along the jacket lumen 138, and the lead liner 140 can include a lead liner lumen 142. The lead 106 can be inserted within the lead liner lumen 142.

The sheath 102 can include a pull wire 148 that is disposed within a pull wire cavity 144 of the sheath 102. A pull wire liner 146 can be disposed between the pull wire 148 and the pull wire cavity 144 to reduce friction between the pull wire 148 and the jacket 136. The dimension of the pull wire 148 can be less than a dimension of the pull wire liner 146 to provide clearance. The sheath 102 in the example of FIG. 3 can be steerable. For instance, compression or tension force can be applied to the pull wire 148 to bend the sheath 102 along a bend plane 166. In other words, the bend plane can be located along a neutral axis or plane of bending through the cross section of the sheath.

Signal wires 158A, B can be electrically coupled between the respective electrodes 128A, B and the ECU 116. The signal wires 158A, B can be constructed from a conductive wire or trace. In some examples, the signal wire 158A, B can be constructed from a copper wire, such as a braided copper wire, or can be a printed copper trace, such as a printed copper trace disposed on a flexible circuit. In the example of FIG. 3, the signal wires 158A, B can be located along or near the bend plane 166 of the sheath 102. Accordingly, strain on the signal wires 158A, B can be reduced as the sheath 102 is bent during navigation of the sheath 102 and the lead 106. In some examples, the signal wire 158A, B can include signal wire insulation 156A, B. The signal wire 158A, B can be located within a respective signal wire liner lumen 154A, B of a signal wire liner 152A, B. The signal wire liner 152A, B can be located within a respective signal wire lumen 150A, B.

The lead liner 140 and signal wire liners 152A, B can include a material with lubricious characteristics to reduce friction between the jacket 136 and the respective lead 106 and signal wires 158A, B. For instance, the lead liner 140 and signal wire liners 152A, B can be constructed from a polymer, such as Polytetrafluoroethylene (PTFE).

FIG. 3 depicts an example of the location of the cut path 134. In some instances, the travel of the blade 132 along the sheath 102 can be unpredictable or irregular. If the blade 132 cuts into the signal wire liner 152A, B, the signal wire insulation 156A, B, or the signal wire 158A, B, the electrical connection of the signal wire 158A, B can be degraded or severed. In another example, a piece of the signal wire liner 152A, B, the signal wire insulation 156A, B, or the signal wire 158A, B can be sliced off from the sheath 102 creating debris. In some examples, debris could enter the body of the patient, for instance, the debris could fall into the incision through which the sheath 102 is inserted into the body. Due to manufacturing constraints, the internal elements of the sheath 102 are not always sterilized.

The sheath 102 can include a cut protection means, such as a means for shielding the signal wires 158A, B, the pull wire 148, the respective liners 152A, B and 146 or a combination thereof from damage from the blade 132 during the cutting process. In the example of FIG. 3, the sheath 102 can include one or more guard rails, such as rails 162A, B to shield the blade 132 from cutting into elements of the sheath 102 that could generate debris, such as the signal wire liner 152A, B, the signal wire insulation 156A, B, or the signal wire 158A, B. The rails 162A, B can be located within respective rail lumens 160A, B within the jacket 136. The rails 162A, B can guide the blade 132 along a desired cut path 134 or within a desired cut zone in the sheath 102. The cut path 134 or cut zone can be clear of other elements of the sheath 102, such as the signal wire liner 152A, B, the signal wire insulation 156A, B, the signal wire 158A, B, the pull wire liner 146 or the pull wire 148. The rails 162A, B can be constructed from a cut resistant material, such as a material having a hardness that is similar to or harder than the material of the blade 132. For instance, in an example, the rails 162A, B can be constructed from stainless steel, such as a high strength stainless steel or a hardened stainless steel. In other examples, the rails 162A, B can be constructed from various materials such as polymers (e.g., Para-Aramid, liquid-crystalline polyoxazole [PBO], liquid crystal polymer [LCP], or the like), ceramics, or other. As shown in the example of FIG. 3, the rails 162A, B can be uncoated and the rail lumen 160A, B can be unlined to mitigate debris generation if the cut path 134 of the blade 132 intersects with the rails 162A, B. In an example, the rails 162A, B can include a solid cross section, as opposed to a braided cross section, to reduce the potential for debris generation. Although FIG. 3 depicts two rails 162A, B having circular cross sections, other rail shapes and quantities are contemplated within the scope of this disclosure.

In a further example, the sheath 102 can include jacket stripe 164. The jacket stripe 164 can include a different material than the jacket 136. For instance, the jacket stripe 164 can include material that is easier for the blade 132 to cut through. In an example, the jacket 136 can include a material such as a 75 durometer polymer. The jacket stripe 164 can include lower durometer material than the jacket 136, such as a 35 durometer material. Accordingly, the blade 132 is urged to travel along a cut path that follows the lower path of resistance of the jacket stripe 164. In the example of FIG. 3, the jacket stripe 164 is located at a 90 degree radial from the bend plane 166. In other examples, the sheath 102 can include two jacket stripes, such as symmetrically placed and diametrically opposed jacket stripes.

Figures 4, 5:
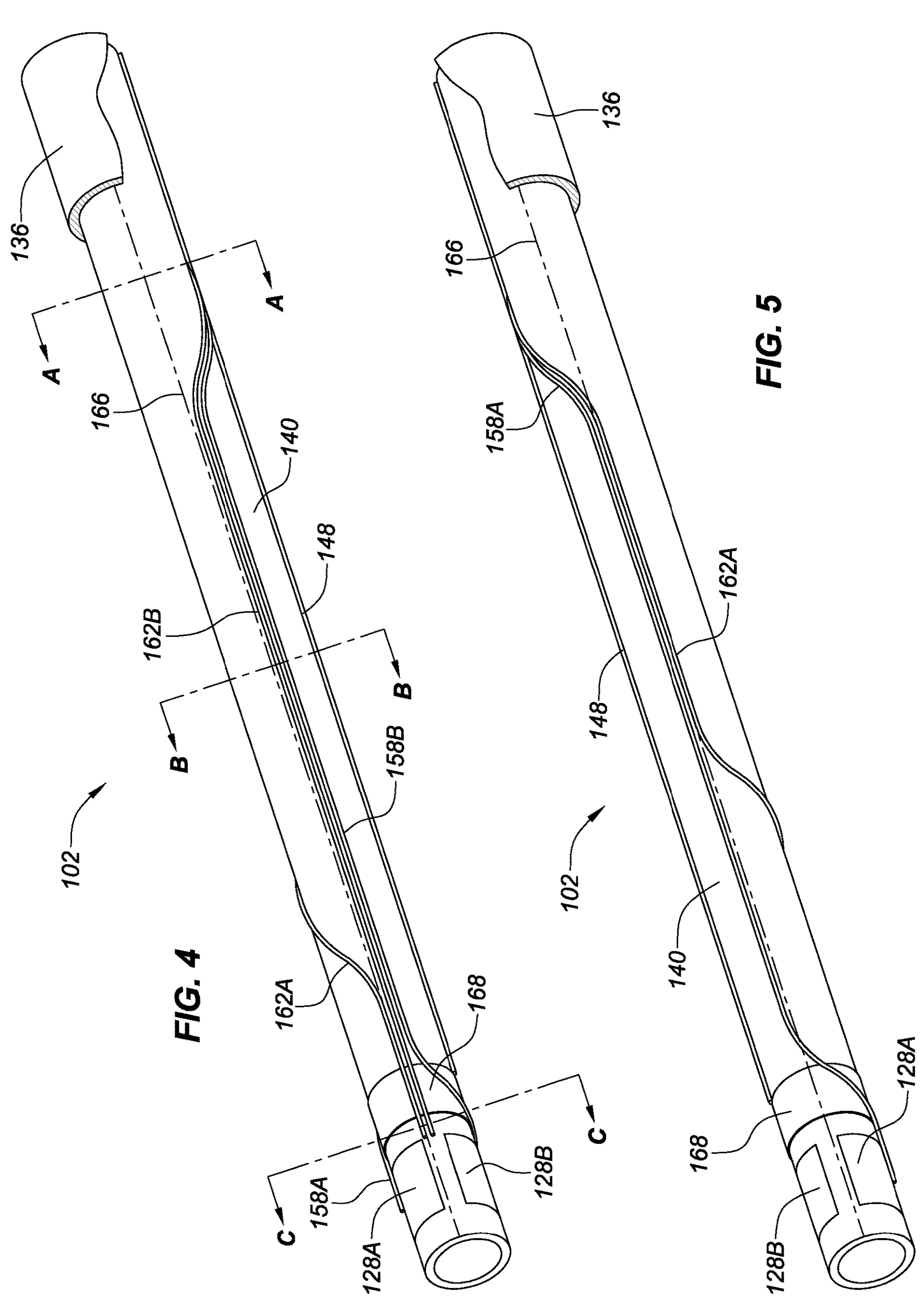
FIG. 4 depicts an isometric view of an example of a first side of a portion of the sheath illustrated with a majority of a jacket removed
FIG. 5 depicts an isometric view of an example of an opposing, second side, of the sheath of FIG. 4.

FIGS. 4 and 5 depict a portion of the sheath 102 in isometric view with a majority of the jacket 136 removed to illustrate the exposed lead liner 140, signal wires 158A, B, and rails 162A, B. FIG. 4 illustrates a first side of the sheath 102, and FIG. 5 depicts an opposing, second side, of the sheath 102. The electrodes 128A, B can include partial rings around the outer diameter of the lead liner 140. For instance, the electrodes 128A, B include a c-shape and can be diametrically opposed about the bend plane 166. The pull wire 148 can be located along the sheath 102 at a 90° radial from the bend plane 166, as shown in the examples of FIGS. 3-5. For instance, the pull wire 148 can be aligned with a center of the electrode 128B. The sheath 102 can include a pull ring 168 located proximally of the electrodes 128A, B. The location of the pull ring 168 can be fixed within the sheath 102 to provide mechanical attachment and support for the pull wire 148.

Figures 10, 11:
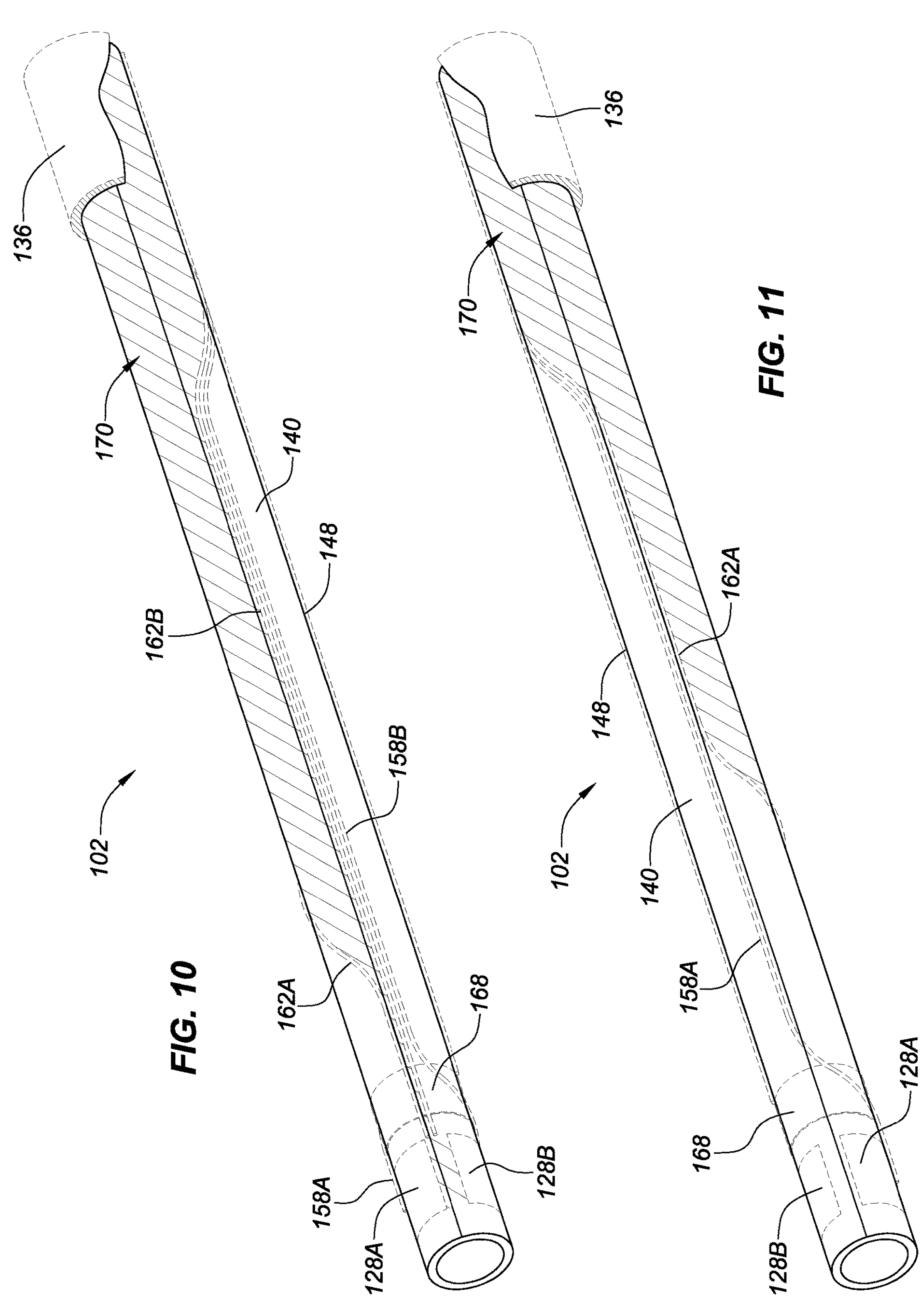
FIGS. 10 and 11 illustrate examples of a cut zone located between a first rail and a second rail.

The first signal wire 158A can electrically couple the electrode 128A to the ECU 116, and the second signal wire 158B can electrically couple the electrode 128B to the ECU 116. As shown in the example of FIGS. 4 and 5, the cut protection means can include the first rail 162A and the second rail 162B. The signal wires 158A, B can be located between the rails 162A, B along the length of the sheath 102. A cut zone can be located in a radial portion of the sheath 102 between the first rail 162A and the second rail 162B, where the radial portion opposes the location of the signal wires 158A, B, as shown in the example of FIGS. 10 and 11.

The rails 162A, B can be fixedly attached to the sheath 102 at the distal end. In an example, the rails 162A, B can be coupled to the pull ring 168. In Another example, the distal end of the rails 162A, B can be molded into the jacket 136. At the proximal end, the rails 162A, B can be free floating, such as free floating within the handle 104. The proximal end of the rails 162A, B can include a stopper to prevent the proximal end of the rails 162A, B from sliding into the respective rail lumens 160A, B.

Figure 6:
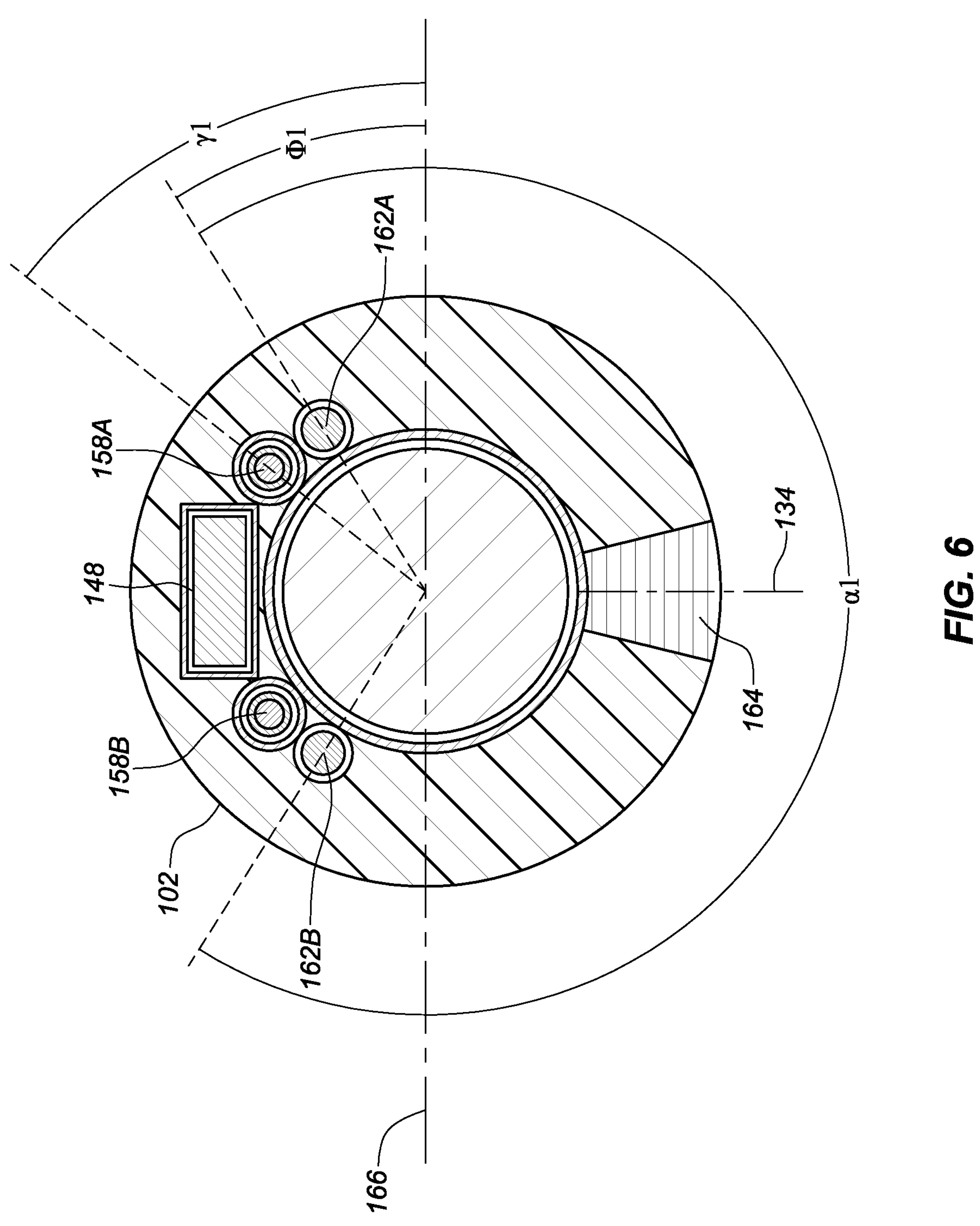
FIG. 6 illustrates an example of a first cross section of the sheath of FIG. 4.
Figure 7:
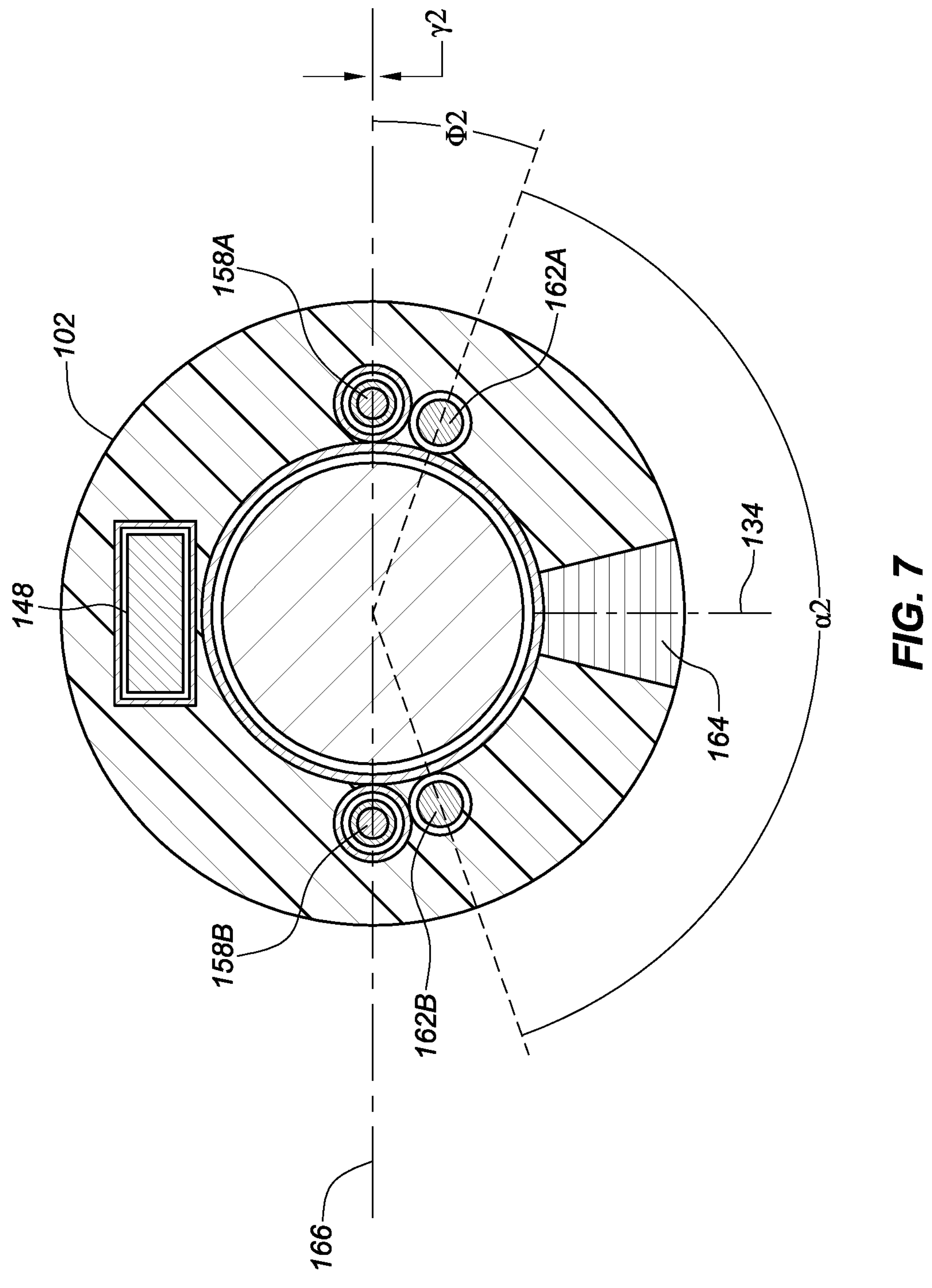
FIG. 7 illustrates an example of a second cross section of the sheath of FIG. 4.
Figure 8:
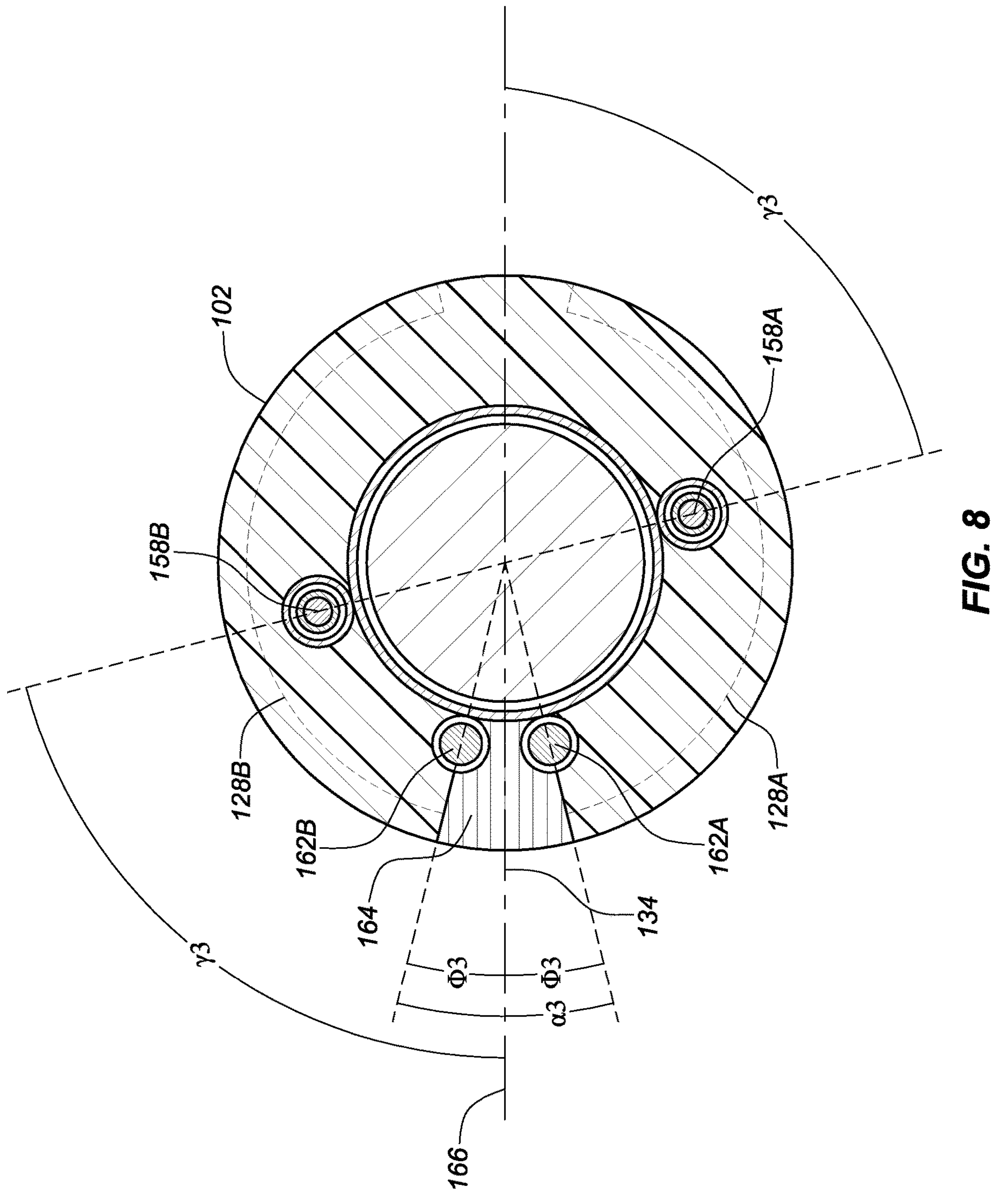
FIG. 8 illustrates an example of a third cross section of the sheath of FIG. 4.

The radial locations (e.g., as measured from the bend plane 166) of the various signal wires 158A, B and rails 162A, B can vary along the length of the sheath 102. For instance, cross sections A-A, B-B, and C-C depicted in the respective FIGS. 6-8 illustrate the various radial locations of the signal wires 158A, B; rails 162A, B; and pull wire 148 at different locations along the longitudinal direction of the sheath 102. In some examples, the cross section A-A can correspond to the section 124A; the cross section B-B can correspond to the sections 124B, C, D, or E; and the cross section C-C can correspond to the section 124F or G.

FIG. 6 illustrates a cross section of the sheath 102 at location A-A, the respective signal wires 158A, B can be positioned at a first radial offset angle $\gamma 1$ with respect to the bend plane 166. In some examples, the first radial offset angle $\gamma 1$ can include a value between 10 and 85 degrees, preferably between 30 and 70 degrees, more preferably between 50 and 60 degrees, or other values therebetween. The respective rails 162A, B can be positioned at a second radial offset angle $\Phi 1$ with respect to the bend plane 166. In some examples, the second radial offset angle $\Phi 1$ can include a value between 10 and 80 degrees, preferably between 30 and 65 degrees, more preferably between 50 and 60 degrees, or other values therebetween. For instance, in the example of FIG. 6, the signal wires 158A, B can be positioned at a one o'clock and an eleven o'clock position respectively. The rails 162A, B can be positioned at a two o'clock and a ten o'clock position respectively. The cut zone can include a radial cut zone angle $\alpha 1$ as measured between the first rail 162A and the second rail 162B. For instance, in the example of FIG. 6, the cut zone angle $\alpha 1$ can include a value between 45 and 270 degrees, preferably between 300 and 330 degrees, and more preferably between 270 and 350 degrees, or other angles. Accordingly, the blade 132 can cut along the cut path 134 at a location within the radial cut zone angle $\alpha 1$ between the first rail 162A and the second rail 162B. In other words, the arrangement of the signal wires 158A, B; rails 162A, B; and pull wire 148 can provide a larger cut zone at the proximal portion of the sheath 102 than at other cross sections (e.g., cross sections B-B or C-C). For instance, the larger cut zone can provide for a larger area for inserting the blade 132, for example, to increase the possibility of inserting the blade into the cut zone and mitigate the possibility of accidental insertion outside of the cut zone where the sheath 102 can be damaged.

FIG. 7 illustrates a cross section of the sheath 102 at location B-B. In some examples, strain (e.g., as a result of bending the sheath 102) can be reduced on the signal wires 158A, B by routing the signal wires 158A, B along or near the bend plane 166. Accordingly, when the sheath 102 is bent by the pull wire 148 for steering the lead 106 to a target location within the body (e.g., the His bundle 114), the strain applied to the signal wires 158A, B can be reduced. Positioning the signal wires 158A, B; rails 162A, B; or both closer to the bend plane 166 as compared to the respective positions at cross section A-A, can reduce the bend resistance of the sheath 102. For example, the signal wires 158A, B; rails 162A, B; or both are strained less when the respective positions are located nearer to the bend plane 166, and accordingly, the amount of force (e.g., tension applied to the pull wire 148) required to bend the sheath 102 can be reduced.

At section B-B, the respective signal wires 158A, B can be positioned at a first radial offset angle γ2 with respect to the bend plane 166. In some examples, the first radial offset angle γ2 can include a value between 0 and 45 degrees, preferably between 0 and 20 degrees, more preferably between 0 and 10 degrees, or other values therebetween. In the example of FIG. 7, the first radial offset angle γ2 is depicted at zero degrees. The respective rails 162A, B can be positioned at a second radial offset angle Φ2 with respect to the bend plane 166. In some examples, the second radial offset angle Φ2 can include a value between 0 and 45 degrees, preferably between 0 and 30 degrees, more preferably between 0 and 15 degrees, or other values therebetween. For instance, in the example of FIG. 7, the signal wires 158A, B can be positioned at a three o'clock and a nine o'clock position respectively. The rails 162A, B can be positioned at a four o'clock and an eight o'clock position respectively. The cut zone can include a radial angle α2 as measured between the first rail 162A and the second rail 162B. For instance, in the example of FIG. 7, the cut zone angle α2 can include a value between 90 and 210 degrees, preferably between 120 and 180 degrees, or other angles. Accordingly, the blade 132 can cut along the cut path 134 at a location within the radial cut zone angle α2 between the first rail 162A and the second rail 162B.

FIG. 8 illustrates a cross section of the sheath 102 at location C-C. The signal wires 158A, B can be routed toward the respective electrodes 128A, B to facilitate the electrical coupling of the signal wires 158A, B to the respective electrodes 128A, B. In some examples, the electrical characteristics of the electrodes 128A, B can be improved by electrically coupling the signal wires 158A, B to the center of the respective electrodes 128A, B. For instance, coupling the signal wires 158A, B at or near the center of the electrodes 128A, B can tune the electrodes 128A, B for improved signal detection, reduced impedance, or the like. Accordingly, the distal end of the signal wires 158A, B can be routed to respective locations along the sheath 102 that are at or near 90 degrees from the bend plane 166 (e.g., where the centers of the respective electrodes 128A, B are located in the example of FIGS. 1-8).

In the example of FIG. 8, the respective signal wires 158A, B can be positioned at a first radial offset angle γ3 with respect to the bend plane 166. In some examples, the first radial offset angle γ3 can include a value between 10 and 90 degrees, preferably between 45 and 90 degrees, more preferably between 75 and 90 degrees, or other values therebetween. For instance, in the example of FIG. 8, the signal wires 158A, B can be positioned at a five o'clock and an eleven o'clock position respectively.

The respective rails 162A, B can be positioned at a second radial offset angle Φ3 with respect to the bend plane 166. In some examples, the second radial offset angle Φ3 can include a value between 0 and 5 degrees, preferably between 0 and 15 degrees, more preferably between 0 and 30 degrees, or other values therebetween. For instance, the rails 162A, B can be positioned at an eight o'clock and a ten o'clock position respectively. The cut zone can include a radial cut zone angle α3 as measured between the first rail 162A and the second rail 162B. For instance, in the example of FIG. 8, the cut zone angle α3 can include a value between 5 and 10 degrees, preferably between 10 and 30 degrees, more preferably between 30 and 60 degrees, or other angles. Accordingly, the blade 132 can cut along the cut path 134 at a location within the radial cut zone angle α3 between the first rail 162A and the second rail 162B.

As further shown in the example of FIG. 8, the cut path 134 at the distal end of the sheath 102 can be located between the electrodes 128A, B. Accordingly, the rails 162A, B can protect the electrodes 128A, B from damage by the blade 132 and further generation of debris caused by cutting one or more of the electrodes 128A, B. It should be understood that the radial locations of the signal wires 158A, B; the rails 162A, B; and the pull wire 148 can remain constant along the length of the sheath 102. For instance, the signal wires 158A, B; the rails 162A, B; and the pull wire 148 can include the radial locations depicted in FIG. 8 along the entire length of the sheath 102. In a further example, it should be understood that any of the examples discussed herein can be implemented with or without the pull wire 148, pull wire liner 146, or pull wire cavity 144.

Figure 9:
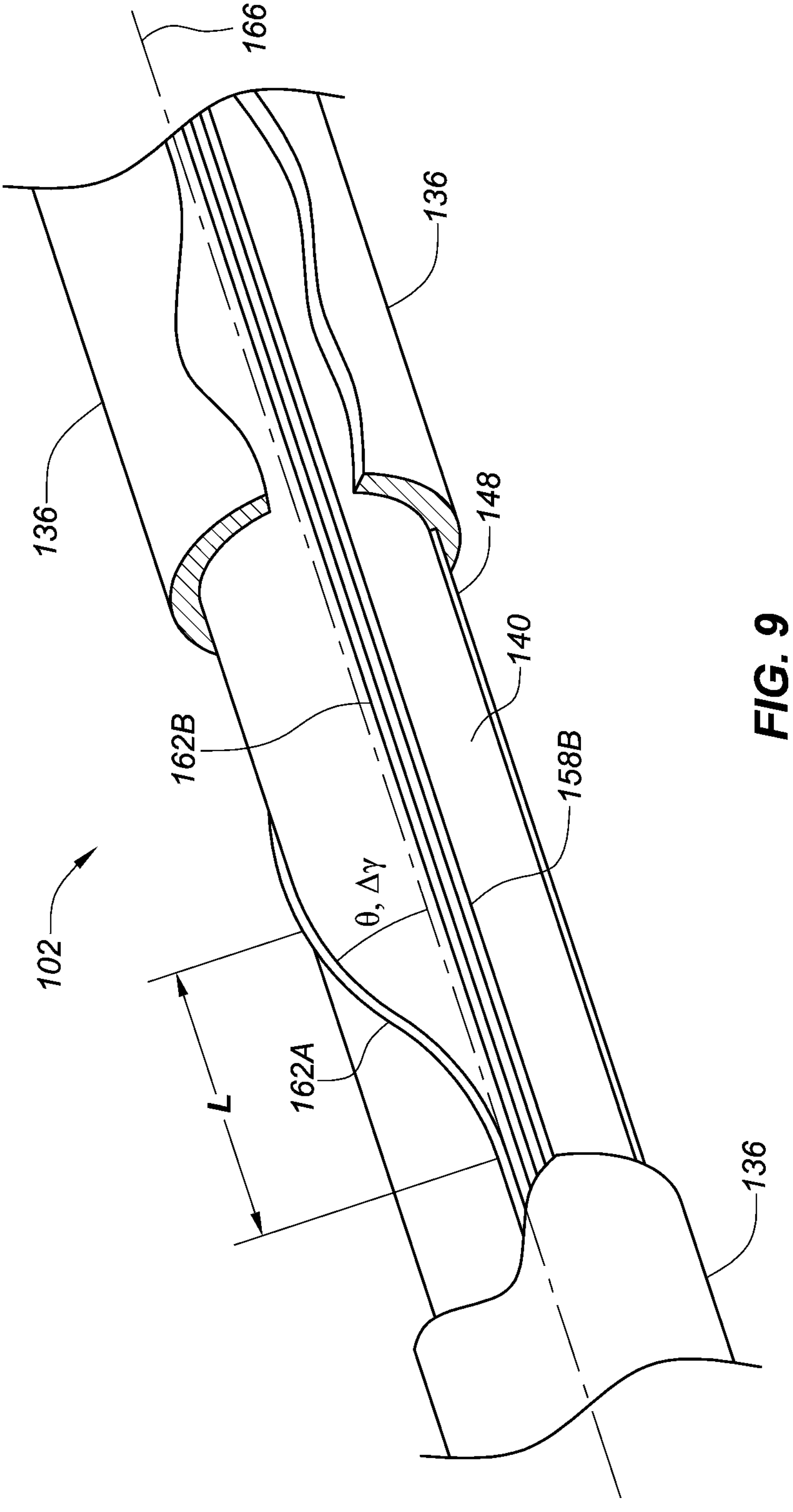
FIG. 9 depicts a detailed view of an example of a portion of the sheath located between the second and the third cross sections of FIG. 4.

FIG. 9 depicts an example of a portion of the sheath 102, such as a portion located between the cross sections B-B and C-C shown in the examples of FIGS. 4, 5, 7 and 8. A portion of the jacket 136 is removed to show the positions of the various signal wires 158A, B and rails 162A, B. As shown in this example, the rail 162A transitions along the longitudinal direction of the sheath 102 from a first radial position to a second radial position. For instance, at the first radial position, the rail 162A can be located at a radial offset angle of about 90 degrees from the bend plane 166, or in other words, at the top (e.g., twelve o'clock noon position) of the sheath 102. At the second radial position, located at a distance L along the longitudinal direction of the sheath 102 from the first radial position, the rail 162A can be located at or near the bend plane 166 (e.g., rotated 90 degrees from first radial position). Accordingly, the rail 162A can be oriented at a transition angle θ from the bend plane 166. As the transition angle increases, the likelihood that the blade 132 could damage or sever the rail 162 increases. In some examples, shallower transition angles can facilitate easier cutting along the sheath 102. In some examples, the transition angle θ can include a value between 0 and 45 degrees, or preferably between 10 and 25 degrees, or more preferably between 5 and 10 degrees, or at other angles therebetween. Alternatively, the transition angle can be measured by a change in the radial offset angle (e.g., Δγ) of the rail 162A over a distance, such as the distance L, along the sheath 102. In various examples, Δγ/L can include a value between 90 degrees over 1.5 inches, 90 degrees over 2.5 inches, or the like.

In the examples of FIGS. 10 and 11 the cut zone 170 is illustrated between the first rail 162A and the second rail 162B. The jacket 136 is depicted as mostly cut away to illustrate the features of the sheath 102 that are located underneath. The cut zone angle (e.g., cut zone angle α1) at the proximal portion of the sheath 102 (e.g., at or near cross section A-A) can be larger than the cut zone angle (e.g., the cut zone angle α2) at a middle portion of the sheath 102 (e.g., at or near cross section B-B), which can be larger than the cut zone angle (e.g., cut zone angle α3) at the distal end of the sheath 102 (e.g., at or near the cross section A-A). In other words, the cut zone 170 can be large at the proximal end where the blade 132 is inserted into the sheath 102 to start the splitting cut along the cut path. The cut zone 170 can narrow toward the distal end of the sheath 102. Accordingly, the rails 162A, B can funnel (e.g., direct) the blade 132 toward a gap between the first electrode 128A and the second electrode 128B.

As shown in the example of FIGS. 4, 5, 10, and 11, the cut path, and accordingly cut zone 170, can extend through the pull ring 168. In various examples, the pull ring 168 can be separable. For instance, the pull ring can include perforations, breakaway features, or a severable material that can be cut by the blade 132. In an example, the material of the pull ring can include gold or similarly soft material. Accordingly, the blade 132 can cut through the pull ring 168 and through the entire length of the sheath 102 to remove the sheath 102 from the lead 106.

Figure 12:
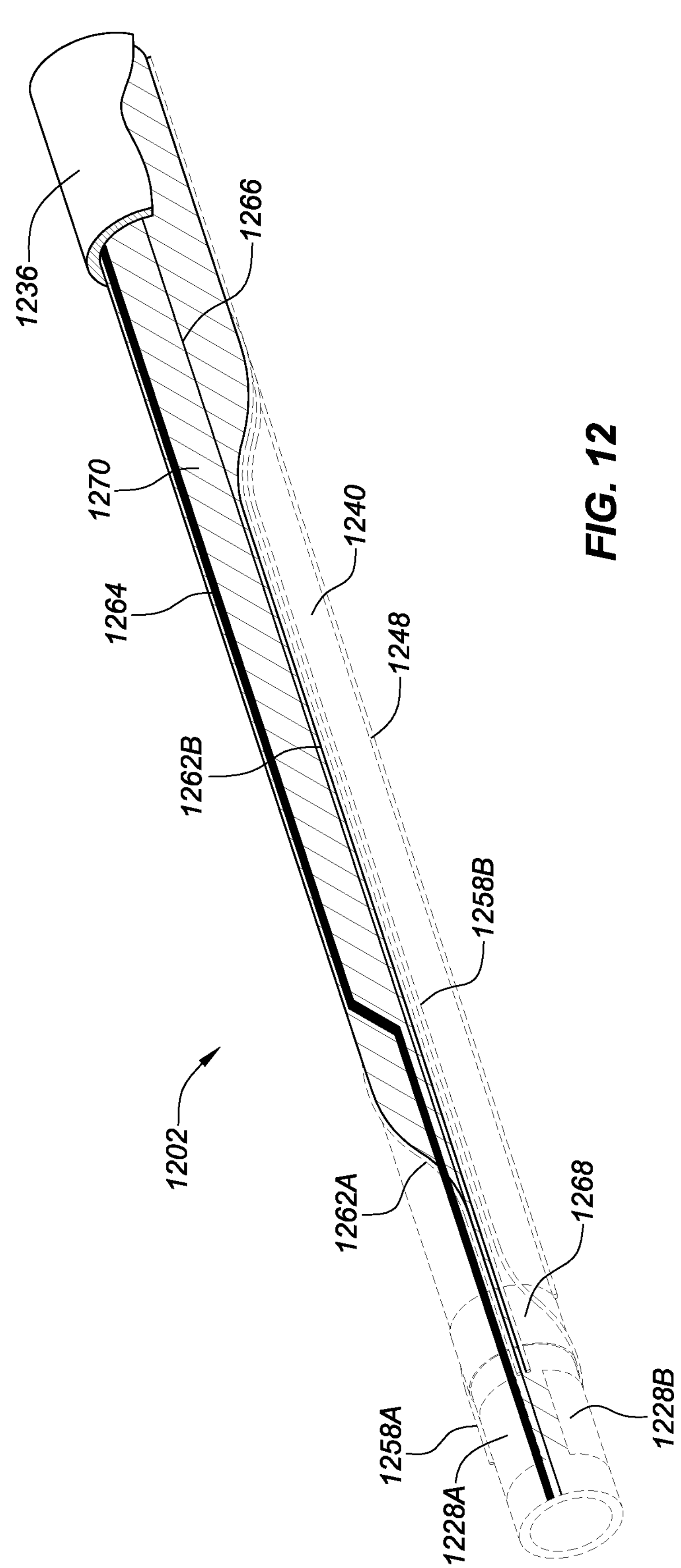
FIG. 12 depicts an example of a jacket stripe located along a cut zone.

FIG. 12, depicts an example of a jacket stripe 1264 located along the cut zone 1270. For instance, the jacket stripe 1264 can be used to guide the blade 132 along the cut path. The jacket stripe 1264 can include a softer material than the jacket 1236 to urge the blade 132 to follow the jacket stripe 1264 along the length of the sheath 1202 during the cutting operation. In some examples, the jacket stripe 1264 can be used independently of the rails (e.g., the rails 162A, B). For instance, the jacket stripe 1264 alone can be the cut protection means. In other examples, the jacket stripe 1264 can be used in combination with the rails (e.g., the rails 162A, B). In further examples, the rails 162A, B can be the cut protection means and can be used independently from the jacket stripe 1264, as illustrated in FIG. 4.

Figure 13:
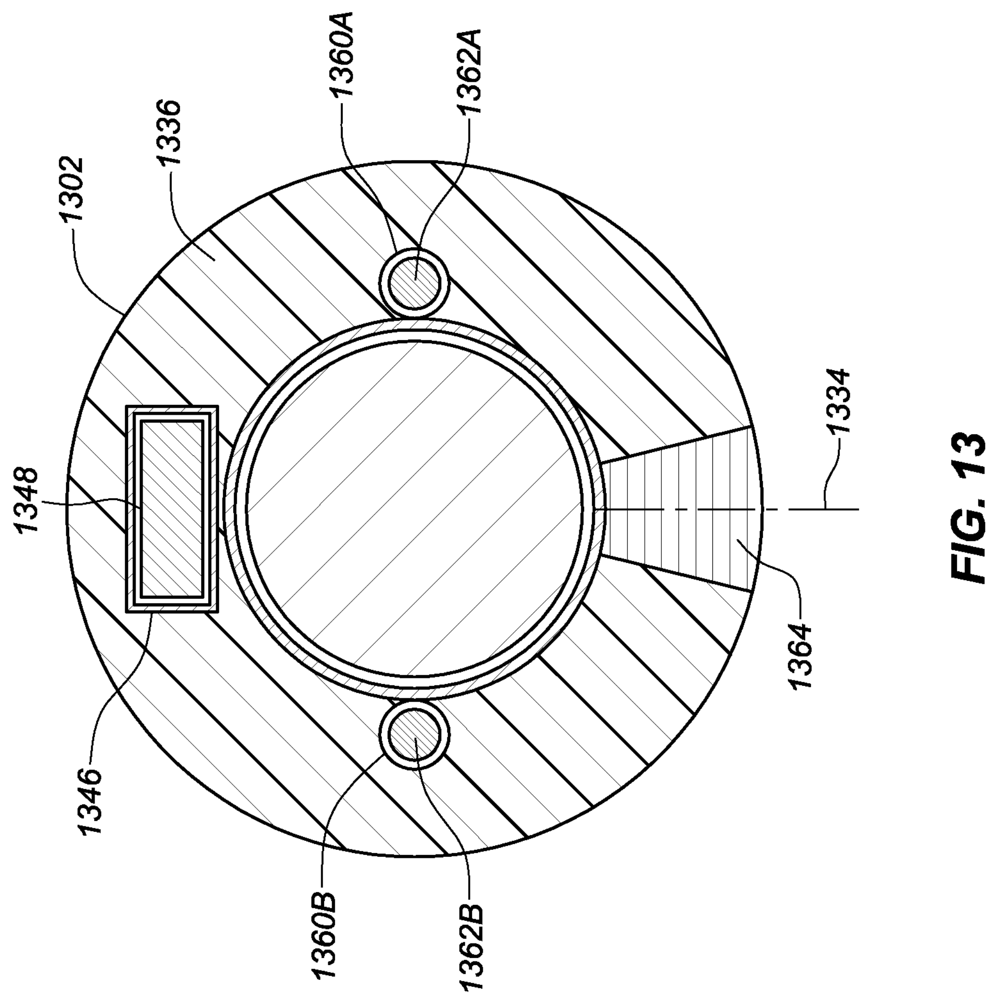
FIG. 13 illustrates an example of a cross section of a sheath including a pull wire, a first rail, and a second rail.

FIG. 13 illustrates a cross section of an example of a sheath 1302 including a pull wire 1348, a first rail 1362A, and a second rail 1362B. The rails 1362A, B can be electrically coupled between the ECU 116 and the respective electrodes (e.g., electrodes 128A, B as shown and described herein). Accordingly, the rails 1362A, B can be used as the signal wires. The rails 1362A, B can be constructed from a cut resistant material, such as a material having a hardness that is similar to or harder than the material of the blade 132. For instance, in an example, the rails 1362A, B can be constructed from steel, stainless steel (e.g., a high strength stainless steel or a hardened stainless steel), or the like. The rails 1362A, B can be located within the respective rail lumens 1360A, B in the jacket 1336. In the example of FIG. 13, the rails 1362A, B can be free of insulation (i.e., bare or uninsulated), and the rail lumens 1360A, B can be free of a liner (i.e., unlined) to mitigate the formation of debris generated by cutting along the sheath 1302 with the blade 132. In some examples, the sheath 1302 can include a jacket stripe 1364 as described further herein.

Figure 14:
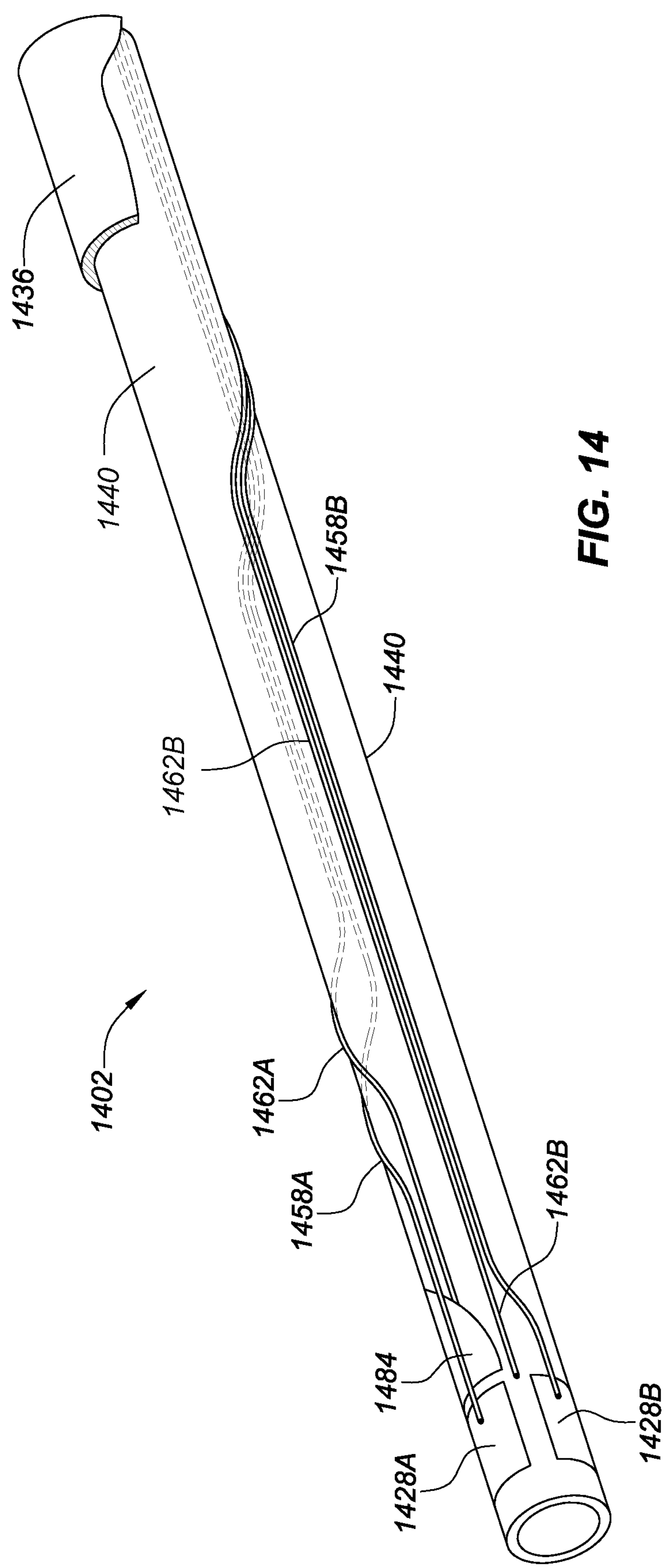
FIG. 14 depicts an example of a sheath including a diverter for guiding a blade around one or more electrodes of the sheath.

FIG. 14 depicts an example of a sheath 1402 including a diverter 1484 for guiding the blade 132 around one or more of the electrodes 1428A, B and shielding the blade 132 from cutting the electrodes 1428A, B and forming debris. The sheath 1402 can include a first signal wire 1458A, a second signal wire 1458B, a first rail 1462A, and a second rail 1462B as described herein. The diverter 1484 can be positioned proximally from the first electrode 1428A. The diverter 1484 can be constructed from a material that resists cutting from the blade 132, such as a material having a hardness that is similar to or harder than the material of the blade 132. For instance, the diverter 1484 can be constructed from a polymer, ceramic, or metal, such as stainless steel (e.g., a high strength stainless steel or a hardened stainless steel). In an example, the diverter 1484 can include a plurality of apertures to aid with retention of the diverter 1484 within the jacket 1436. For instance, when the jacket material is softened or melted during the assembly process, the material can flow into the apertures and provide mechanical fixation when the material cools and hardens. The diverter 1484 can include one or more edges for guiding the blade 132 between the first electrode 1428A and the second electrode 1428B. In an example, the diverter 1484 can include a triangular or wedge shape to guide the blade 132 along a desired cut path. One or more of the rails 1462A, B can be routed to the diverter 1484 and can shield the respective signal wire 1458A, B from the blade 132. In the example of FIG. 14, the various signal wires 1458A, B, and rails 1462A, B can be routed similarly to the examples of FIGS. 4-11. In other examples, the routing of the various signal wires 1458A, B and rails 1462A, B can be simplified when the diverter 1484 is used.

Figure 15:
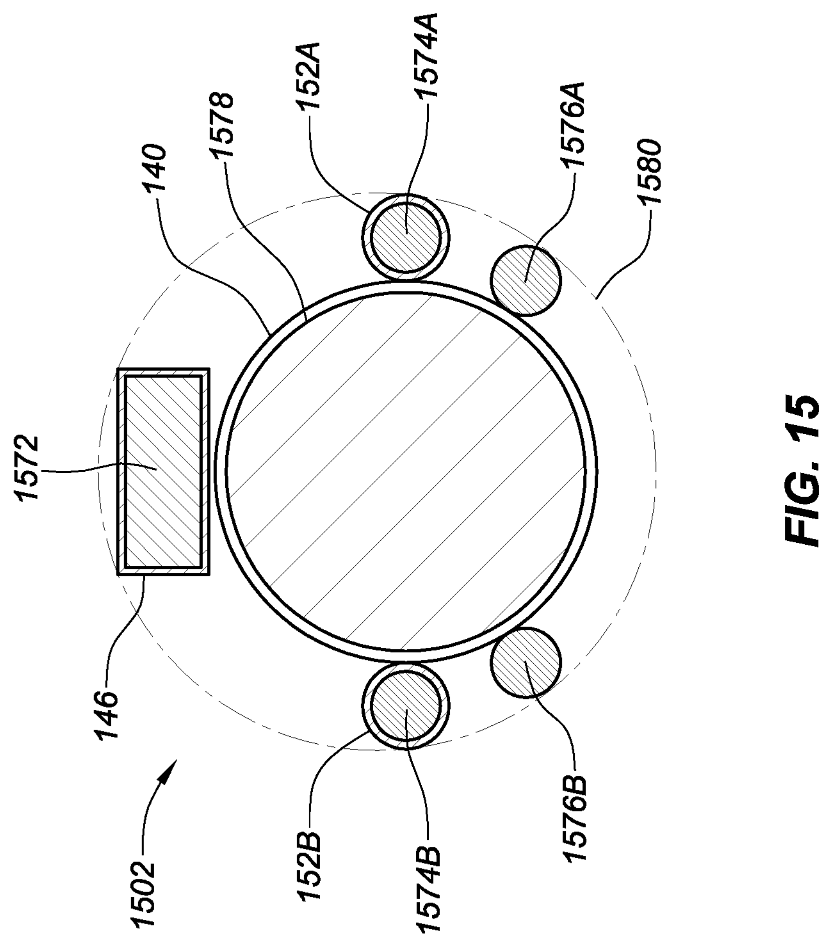
FIGS. 15-17 depict an example of a technique for making a splittable sheath.
Figure 16:
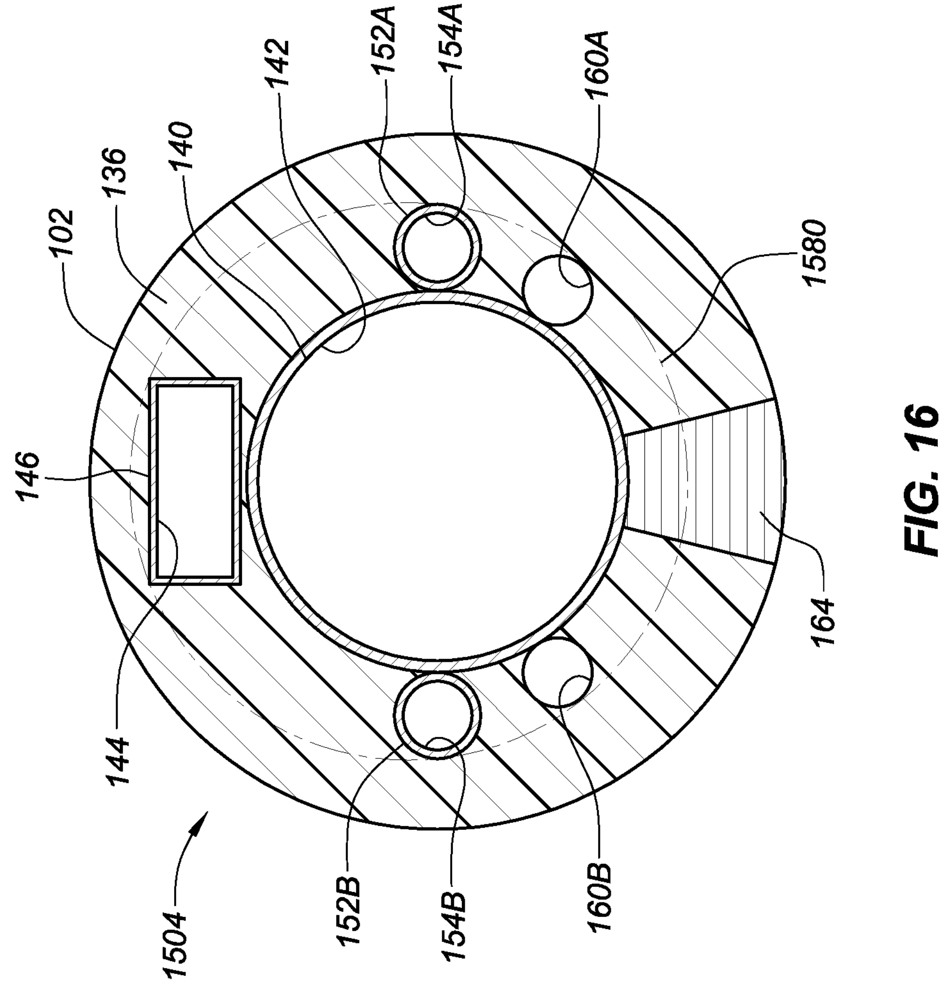
Figure 17:
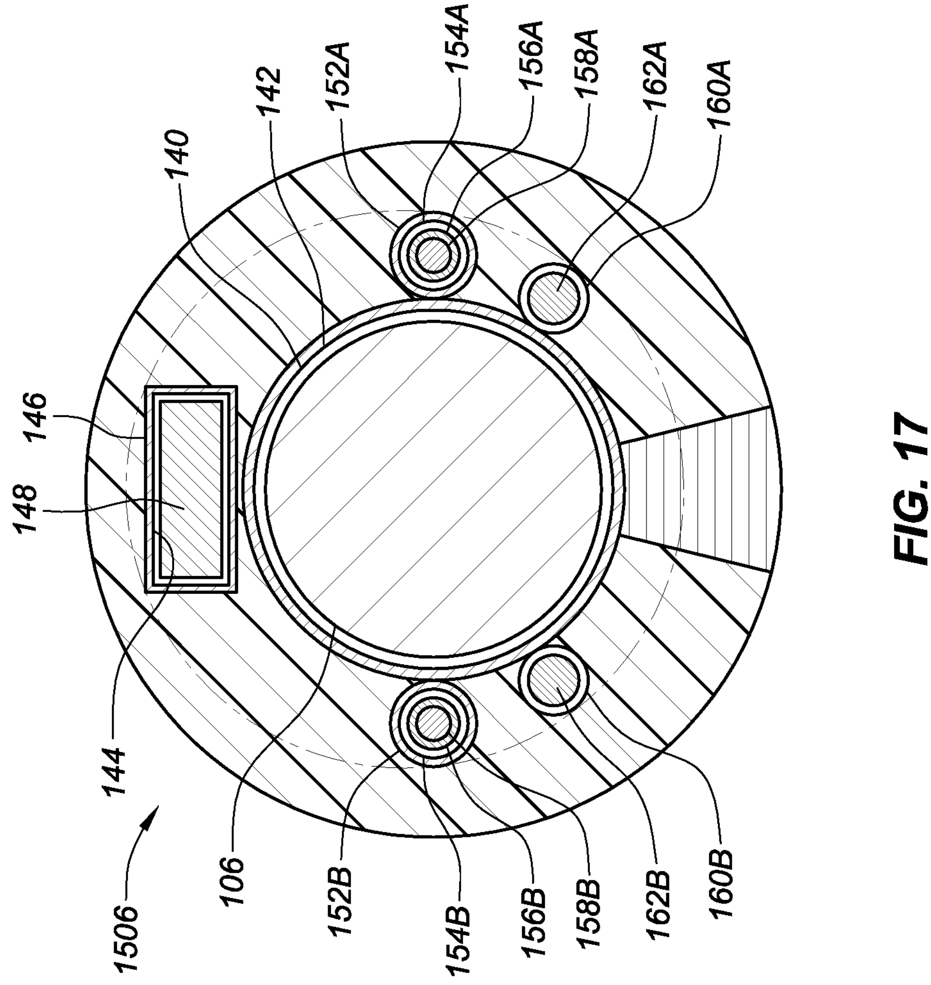

FIGS. 15-17 depict a technique including several steps 1502-1506 for making the splittable sheath 102. As discussed further herein, the sheath 102 can include a cut protection means, such as a plurality of rails 162A, B.

At 1502, the lead liner 140 can be placed over a lumen mandrel 1578; one or more signal wires liners, such as the signal wire liners 152A, B can be placed over respective signal wire mandrels 1574A, B; and a pull wire liner 146 can be placed over a pull wire mandrel 1572. The signal wire liners 152A, B, supported by the respective signal wire mandrels 1574A, B; the pull wire liner 146, supported by the pull wire mandrel 1572; and one or more rail mandrels 1576A, B can be located along an outer diameter (or dimension) of the lead liner 140. In an example, the signal wire liners 152A, B; pull wire liner 146; and the rail mandrels 1576A, B can be removably fixated along the lead liner 140. For instance, the signal wire liners 152A, B; pull wire liner 146; and the rail mandrels 1576A, B can be attached to the lead liner 140 using an adhesive, such as Cyanoacrylate or other adhesive. In some examples, the pull wire mandrel 1572, lumen mandrel 1578, and signal wire mandrels 1574A, B can be constructed of steel or stainless steel, such as a hardened stainless steel. In an example, the pull wire mandrel 1572, lumen mandrel 1578, and signal wire mandrels 1574A, B can be uncoated. In further examples, the lumen mandrel 1578 can be an M7 mandrel and the signal wire mandrels can include a diameter of 0.007 inches.

In an example, the lead liner 140, signal wire liners 152A, B, and pull wire liner 146 can include a lubricious material, for instance, a polymer, such as Polytetrafluoroethylene (PTFE). In some examples, the rail mandrels 1576A, B can include PTFE coated stainless steel wires.

A braid 1580 can be disposed around the various elements depicted in FIG. 15, such as the pull wire liner 146; the signal wire liners 152A, B; and the rail mandrels 1576A, B. The braid 1580 can provide stability to sheath 102. The braid 1580 can include multi-thread metallic wires that can be woven with a regular, full load pattern (with one wire passing under two wires and then over two wires), a diamond pattern (with two side by side wires alternately passing under two side by side wires then over two side by side wires), a half load diamond pattern (with one wire passing under one wire and then over one wire) or other patterns known in the art. In some examples, the multi-thread metallic wires can be be round, with diameters of from about 0.02 mm to about 0.2 mm, or flat, with sizes ranging from about 0.01 mm thick by about 0.05 mm wide to about 0.1 mm thick by about 0.20 mm wide.

At step 1504, illustrated in FIG. 16, the jacket 136 can be applied over the braid 1580; the pull wire liner 146; the signal wire liners 152A, B; and the rail mandrels 1576A, B. The jacket 136 can include a polymer, such as a thermoplastic elastomer, such as polyamide (e.g., nylon 11, nylon 12, nylon 612, and the like), polyesters (e.g., poly(butylene terephthalate), poly(ethylene terephthalate), and the like), thermoplastic elastomers (e.g., poly(ether block amide) copolymer resins, poly(ether co ester) block copolymer resins), and various thermoplastic polyurethane block copolymer resins. The jacket 136 can provide columnar strength in the proximal and middle portions of sheath 102 and deflectability in the distal portion of the sheath 102.

In some examples, the jacket 136 can be extruded over the braid 1580; the pull wire liner 146; the signal wire liners 152A, B; the rail mandrels 1576A, B; and the lead liner 140. In some examples, the jacket 136 can include an extruded profile, or a plurality of extruded profiles that are placed over the braid 1580; the pull wire liner 146; the signal wire liners 152A, B; the rail mandrels 1576A, B; and the lead liner 140. The assembly of the extruded profiles, braid 1580; pull wire liner 146; pull wire mandrel 1572; signal wire liners 152A, B; signal wire mandrels 1574; rail mandrels 1576A, B; lead liner 140; and lumen mandrel 1578 can be heated (for example in a reflow oven) to fuse the one or more of the extruded profiles around the braid 1580; pull wire liner 146; signal wire liners 152A, B; rail mandrels 1576A, B; and lead liner 140.

As shown in the example of FIG. 1, the sections 124A-G can be comprised of various extruded profiles corresponding to the respective materials along the sections 124A-G (e.g., 75 durometer, 55 durometer, 40 durometer, or 35 durometer). The various extruded sections 124A-G can be fused using the reflow oven. The various sections 124A-G can be interposed along the distal portion of the sheath 102. As described above, the sections 124A-G can include materials having different material properties, such as materials having different moduli of elasticity, moduli of flexure, or hardness to provide one or more hinge points along the lead 106. For instance, the section 124A can include a material having a durometer of 75; sections 124B, D, F can include a material having a durometer of 55; sections 124C, E can have a durometer of 35; and the distal section 124G can have a durometer of 40. Each of the various sections 124A-G can be joined to one or more of the other respective sections 124A-G by gluing, ultrasonic welding, reflow heating, or other techniques. In a preferred arrangement, the distal section 124G can be formed from a polymer that is softer than the material forming sections 124A, B, D, F so as to provide an atraumatic tip to the sheath 102.

In another example, the jacket 136 can be comprised of multiple layers. A first thermoplastic polymer can be formed onto the pull wire liner 146; signal wire liners 152A, B; rail mandrels 1576A, B; and lead liner 140. The braid 1580 can then be placed over the first thermoplastic polymer layer. A second thermoplastic polymer layer can be applied over the first thermoplastic polymer layer. The thermoplastic polymers forming the respective first and second thermoplastic polymer jacket layers can be the same, similar, or different. However, they should be chemically compatible or miscible so that the polymer of the second thermoplastic polymer layer (e.g., the outer jacket layer) strongly adheres to the first thermoplastic polymer layer (e.g., the inner jacket layer) as it is extruded or fused thereover. This strong adherence may be achieved by using a polymer with a relatively lower melt temperature for the first thermoplastic polymer layer and a polymer with a relatively higher melt temperature for the second thermoplastic polymer layer. As a result, the polymer of the second thermoplastic polymer layer will thermally fuse and strongly adhere to the first thermoplastic polymer layer, embedding the braid 1580 therebetween.

In further examples, the first thermoplastic polymer may be formed onto the lead liner 140. The pull wire liner 146; signal wire liners 152A, B; and rail mandrels 1576A, B can then be positioned along the lead liner 140. In some instances, the pull wire liner 146; signal wire liners 152A, B; rail mandrels 1576A, B can be attached to the lead liner 140 using an adhesive as described further herein. The braid 1580 can then be placed over the first thermoplastic polymer layer and a second thermoplastic polymer layer can be applied over the first thermoplastic polymer layer.

In some examples, the jacket 136 can include the jacket stripe 164. The jacket stripe 164 can include a different material than the jacket 138. In various examples, the jacket stripe 164 can be extruded along with the jacket material or, in other examples, the jacket stripe 164 can be included in one or more extruded profiles, which are then fused, as previously described. In the example of FIG. 16, the jacket stripe 164 is located at a 90 degree radial from the bend plane 166. In other examples, the sheath 102 can include two jacket stripes, such as symmetrically placed and diametrically opposed jacket stripes. The symmetrically opposing jacket stripes can facilitate uniform extrusion, for instance, by reducing inconsistent shrinkage or unsymmetrical distortions during the application of the jacket 136. The jacket stripe 164 can include material that is easier for the blade 132 to cut through. In an example, the jacket 136 can include a material such as a 75 durometer polymer. The jacket stripe 164 can include lower durometer material than the jacket 136, such as a 35 durometer material. Accordingly, the blade 132 is urged to travel along a cut path 134 that follows the lower path of resistance of the jacket stripe 164.

In some examples, the jacket 136 may include radiopaque fillers, such as barium sulfate, tungsten, bismuth trioxide, bismuth subcarbonate, bismuth oxychloride and the like. Polymers containing the radiopaque filler can be used in one or more of the various sections 124A-G of the sheath 102. In a further example, the jacket 136 can be sheathed in a sleeve, such as a polyimide sleeve. In some examples, the sleeve can be a shrink wrap tube applied to the jacket 136 during the reflow process.

Once the jacket 136 is applied, the mandrels can be removed. For instance, the pull wire mandrel 1572, lumen mandrel 1578, and the signal wire mandrels 1574A, B can be removed from their respective pull wire liner 146 and signal wire liners 152A, B. The pull wire liner 146, the lead liner 140, and the signal wire liners 152A, B can facilitate the removal of the pull wire mandrel 1572, lumen mandrel 1578, and the signal wire mandrels 1574A, B because of the lubricity of the materials of the pull wire liner 146, lead liner 140, and the signal wire liners 152A, B. Likewise, the rail mandrels 1576A, B can include a PTFE coating to facilitate removal from the rail lumens 160A, B of the jacket 136. Once the pull wire mandrel 1572, lumen mandrel 1578, and the signal wire mandrels 1574A, B, and rail mandrels 1576A, B are removed, the pull wire cavity 144, lead liner lumen 142, signal wire liner lumens 154A, B, and rail lumens 160A, B are prepared for the assembly of the pull wire 148, the lead 106, the signal wires 158A, B, and the rails 162A, B.

At 1506, the pull wire 148, the lead 106, the signal wires 158A, B, and the rails 162A, B can be inserted into the respective pull wire liner cavity 144, lead liner lumen 142, signal wire liner lumens 154A, B, and rail lumens 160A, B as depicted in the example of FIG. 17. For instance, the sheath 102 can include a pull wire 148 that is disposed within the pull wire liner 146 to reduce friction between the pull wire 148 and the jacket 136. The dimension of the pull wire 148 can be less than an inner dimension of the pull wire liner 146 to provide clearance.

The signal wires 158A, B can be inserted into the respective signal wire liner lumens 154A, B of the signal wire liners 152A, B. The signal wires 158A, B can be electrically coupled between the respective electrodes 128A, B and the ECU 116 as shown in the example of FIG. 1 and described further herein. The signal wires 158A, B can be constructed from a conductive wire or trace. In some examples, the signal wire 158A, B can be constructed from a copper wire, such as a braided copper wire, or can be a printed copper trace, such as a printed copper trace disposed on a flexible circuit. As shown in the examples of FIG. 17, the signal wires 158A, B, can be located along or near the bend plane 166. Accordingly, strain on the signal wires 158A, B can be reduced as the sheath 102 is bent during navigation of the sheath 102 and the lead 106. In some examples, the signal wire 158A, B can include signal wire insulation 156A, B. The signal wire 158A, B can be located within a respective signal wire liner lumen 154A, B of a signal wire liner 152A, B. The signal wire liner 152A, B can be located within a respective signal wire lumen 150A, B.

One or more rails 162A, B can be inserted into the respective rail lumens 160A, B. The rails 162A, B can guide a blade along a desired cut path or within a desired cut zone in the sheath 102. The cut path or cut zone can be clear of other elements of the sheath 102, such as the signal wire liner 152A, B, the signal wire insulation 156A, B, the signal wire 158A, B, the pull wire liner 146 or the pull wire 148. The rails 162A, B can be constructed from a cut resistant material, such as a material having a hardness that is similar to or harder than the material of the blade 132. For instance, in an example, the rails 162A, B can be constructed from steel, stainless steel (e.g., a high strength stainless steel or a hardened stainless steel), or the like. In other examples, the rails 162A, B can be constructed from various materials such as polymers (e.g., Para-Aramid, liquid-crystalline polyoxazole [PBO], liquid crystal polymer [LCP], or the like), ceramics, or other. As shown in the example of FIG. 17, the rails 162A, B can be uncoated and the rail lumen 160A, B can be unlined to mitigate debris generation if the cut path 134 of the blade 132 intersects with the rails 162A, B. In an example, the rails 162A, B can include a solid cross section, as opposed to a braided cross section, to reduce the potential for debris generation. Although FIG. 17 depicts two rails 162A, B having circular cross sections, other rail shapes and quantities are contemplated within the scope of this disclosure. Accordingly, the sheath 102 can include a cut protection means, such as a means for shielding the signal wires 158A, B, signal wire liners 152A, B, the pull wire 148, the pull wire liner 146, or combinations thereof from damage from the blade during the cutting and splitting process.

Figures 18, 19:
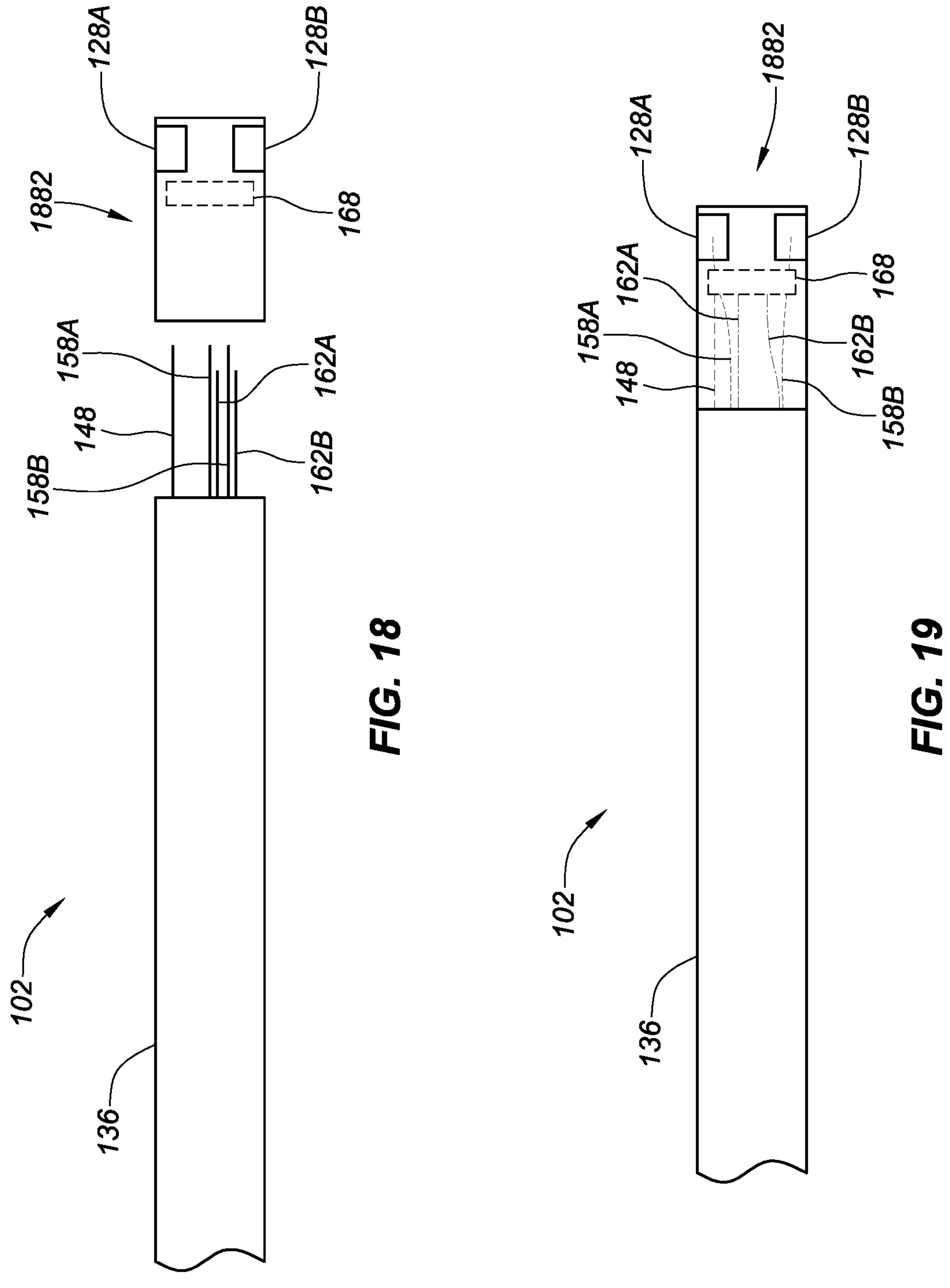
FIG. 18 illustrates an example of a sheath in a partially assembled state.
FIG. 19 depicts an example of a tip portion coupled with the sheath of FIG. 18.

FIG. 18 illustrates an example of the sheath 102 in a partially assembled state. In this example, a tip portion 1882, can be assembled to the remaining portions of the sheath 102 (e.g., a distal portion of the sheath 102). The tip portion 1882 can include the pull ring 168 and the plurality of electrodes 128A, B. Distal portions of the pull wire 148, the signal wires 158A, B, and the rails 162A, B can be extended from a distal portion of the jacket 136, as shown in the example of FIG. 18. As depicted in FIG. 19, the signal wires 158A, B can be electrically coupled to the respective electrodes 128A, B. For instance, the signal wires 158A, B can be soldered, crimped, or otherwise communicatively coupled to the electrodes 128A, B. Pull wire 148 can be mechanically coupled to the pull ring 168. Tip portion 1882 can include a cavity or a plurality of cavities to accommodate the pull wire 148, the signal wires 158A, B and the rails 162A, B. When the pull wire 148, the signal wires 158A, B and the rails 162A, B are inserted into the cavity or respective cavities, the sheath 102 and the tip portion 1882 can be coupled together as shown in the example of FIG. 19. In an example, a reflow oven can be used to fuse the tip portion 1882 to the remainder of the sheath 102 and the jacket 136. In other examples, other methods can be used to melt or fuse the tip portion 1882 to the remaining portions of sheath 102 and jacket 136. In some examples, the rails 162A, B can be coupled to the tip portion 1882 by fusing the tip portion 1882 around the rails 162A, B, mechanically coupling the distal end of the rails 162A, B to the pull ring 168, or a combination thereof.

Figure 20:
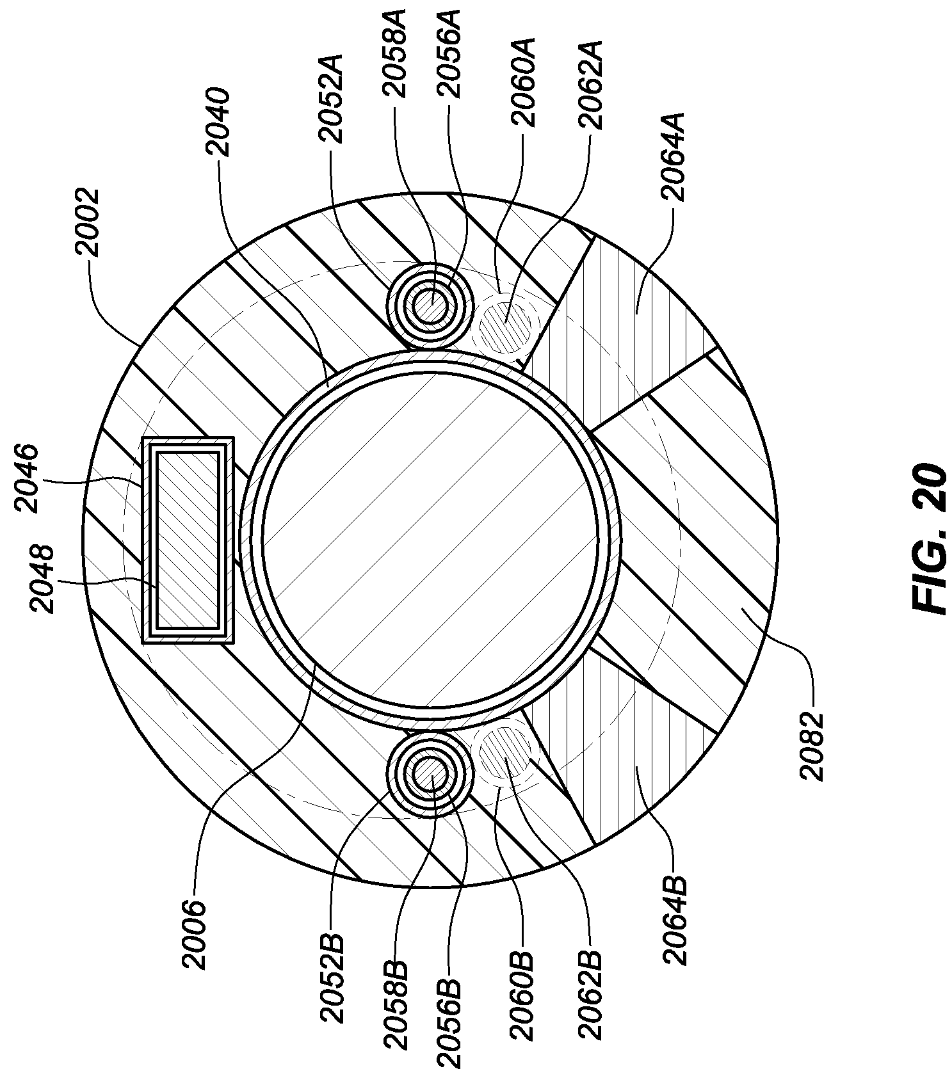
FIG. 20 illustrates an example of a sheath including a plurality of jacket stripes.

FIG. 20 illustrates an example of a sheath 2002 including a plurality of jacket stripes 2064A, B. The sheath 2002 can include a jacket 2036, at least one pull wire 2048, one or more signal wires 2058A, B, and one or more rails 2062A, B as previously described herein. The plurality of jacket stripes can include a first jacket stripe 2064A and a second jacket stripe 2064B. In the example of FIG. 20, the first and second jacket stripes 2064A, B can be infused with an additive to increase the cut resistance of the jacket stripes 2064A, B. For instance, the jacket stripes 2064A, B can be infused with a particulate, such as tungsten, to increase the cut resistance. The blade, such as the blade 132 can be inserted into an intermediary jacket strip 2082 located between the first jacket stripe 2064A and the second jacket stripe 2064B. As depicted in the example of FIG. 20, the first jacket stripe 2064A can be offset from the second jacket stripe 2064B by a radial angle having a value including, but not limited to, between 10 degrees and 270 degrees; preferably between 45 degrees and 180 degrees, more preferably between 90 degrees and 120 degrees. In various examples, the intermediary strip 2082 can include the same material as the remainder of the jacket 2036 or can include a different material, such as a softer material to facilitate splitting the sheath 2002 along the intermediate strip 2082. Because the first jacket stripe 2064A and the second jacket stripe 2064B resist cutting, the blade can be urged to follow along the intermediate strip 2082. Accordingly, the first and second strips 2064A, B can provide a cut prevention means for reducing damage or debris resulting from the blade cutting into the signal wire liner 2052A, B; the signal wire insulation 2056A, B; the signal wire 2058A, B; the pull wire liner 2046; or the pull wire 2048.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A splittable sheath for an implantable medical device, the sheath comprising:
- a jacket including an annular wall extending from a proximal end to a distal end and having an outer diameter and an inner diameter, wherein the annular wall includes a jacket section and a jacket stripe section extending from the proximal end to the distal end, and wherein the jacket stripe section is constructed from a material that is softer than a material of the jacket section;
- a lumen defined by the inner diameter and extended from the proximal end to the distal end of the jacket;
- an electrode located at the distal end of the jacket;
- a signal wire disposed within the jacket and electrically coupled to the electrode; and
- a plurality of guard rails configured to shield the signal wire from a cut path of a sheath splitter, the plurality of guard rails defining a cut zone extending in a longitudinal direction along the jacket, wherein when the splittable sheath is unsplit the cut zone has a radial cut zone angle that is larger at the proximal end than at the distal end of the jacket.

2. The splittable sheath of claim 1, wherein the plurality of guard rails include a first rail separated from a second rail by the radial cut zone angle.

3. The splittable sheath of claim 2, wherein the signal wire is located between the first rail and the second rail along the length of the sheath, and wherein the cut path is located between the first rail and the second rail on a radially opposing side of the sheath from the signal wire.

4. The splittable sheath of claim 3, wherein:
- at the proximal end, the cut zone angle is greater than 270 degrees, and
- at the distal end, the cut zone angle is less than 90 degrees.

5. The splittable sheath of claim 3, wherein the cut zone is defined between the first rail and the second rail on a radially opposing side of the sheath from the signal wire.

6. The splittable sheath of claim 1, wherein the plurality of guard rails are exposed from the jacket at the proximal end.

7. The splittable sheath of claim 1, wherein the plurality of guard rails are constructed from a cut resistant material.

8. The splittable sheath of claim 1, wherein the plurality of guard rails are constructed from stainless steel.

9. The splittable sheath of claim 1, wherein the plurality of guard rails are configured to reduce debris formation caused by contact with the sheath splitter.

10. The splittable sheath of claim 1, wherein the plurality of guard rails include a solid cross section.

11. The splittable sheath of claim 1, wherein the signal wire is located at a bend plane along the cross section of the sheath.

12. The splittable sheath of claim 1, wherein the jacket includes two jacket stripe sections extending from the proximal end to the distal end.

13. The splittable sheath of claim 1, wherein the radial location of the signal wire remains constant along the length of the sheath.

14. The splittable sheath of claim 1, further comprising a pull wire disposed within the jacket, wherein the plurality of guard rails are further configured to shield the pull wire from the cut path.

15. The splittable sheath of claim 1, further comprising a lead disposed within the lumen of the sheath.

16. A splittable sheath for an implantable medical device, the sheath comprising:
- a jacket including an annular wall extending from a proximal end to a distal end and having an outer diameter and an inner diameter, wherein the annular wall includes a jacket section and a jacket stripe section extending from the proximal end to the distal end, and wherein the jacket stripe section is constructed from a material that is softer than a material of the jacket section;
- a lumen defined by the inner diameter and extended from a proximal end to a distal end of the jacket;
- an electrode located at the distal end of the jacket;
- a signal wire disposed within the jacket and electrically coupled to the electrode; and
- a first rail and a second rail each configured to shield the signal wire from a cut path of a sheath splitter, wherein the signal wire is located between the first rail and the second rail along the length of the sheath, wherein the cut path is located between the first rail and the second rail on a radially opposing side of the sheath from the signal wire, the first rail and the second rail each including a longitudinal segment extending in longitudinal direction along the jacket and defining a cut zone between the first rail and the second rail, and wherein when the splittable sheath is unsplit the cut zone has a radial cut zone angle that is larger at the proximal end than at the distal end of the jacket.

17. A method for making a splittable sheath, the method comprising:

placing a lead liner over a lumen mandrel;

placing a signal wire liner over a signal wire mandrel;

locating a first rail mandrel and a second rail mandrel along an outer diameter of the lead liner, wherein the signal wire liner is located between the first rail mandrel and the second rail mandrel along the length of the sheath;

applying a jacket over the signal wire liner and the first and second rail mandrels, wherein the jacket includes an annular wall extending from a proximal end to a distal end, wherein the annular wall includes a jacket section and a jacket stripe section extending from the proximal end to the distal end, and wherein the jacket stripe section is constructed from a material that is softer than a material of the jacket section;

removing each of the lumen mandrel, the signal wire mandrel, and the first and second rail mandrels, after the jacket is applied;

inserting a signal wire into the signal wire liner lumen, a first rail into the first rail lumen, and a second rail into the second rail lumen, after the lumen mandrel, the signal wire mandrel, and the first and second rail mandrels are removed, the first rail and the second rail each including a longitudinal segment extending in a longitudinal direction along the jacket and defining a cut zone between the first rail and the second rail, and wherein when the splittable sheath is unsplit the cut zone has a radial cut zone angle that is larger at the proximal end than at the distal end of the jacket; and electrically coupling the signal wire to an electrode located on a distal end of the jacket.

18. The method of claim 17, further comprising disposing a braid around the signal wire liner and the first and second rail mandrels before applying the jacket, and wherein the jacket is extruded over the braid.

19. The method of claim 17, wherein applying the jacket includes placing an extruded profile over the signal wire liner, the first and second rail mandrels, and the lead liner.

20. The method of claim 19, wherein the extruded profile is heated to fuse the profile around the signal wire liner, the first and second rail mandrels, and the lead liner.

21. The method of claim 17, wherein placing the signal wire lumen includes placing the signal wire lumen along a bend plane of the sheath.

22. The method of claim 17, wherein inserting the first rail and the second rail includes inserting a first rail and a second rail that are constructed of a solid material to reduce debris formation.

23. The method of claim 17, wherein the first rail lumen and the second rail lumen are unlined and the first rail and the second rail are uncoated.

* * * * *